(12) United States Patent
Chang et al.

(10) Patent No.: US 6,706,491 B1
(45) Date of Patent: Mar. 16, 2004

(54) REAGENTS AND METHODS FOR IDENTIFYING AND MODULATING EXPRESSION OF GENES REGULATED BY P21

(75) Inventors: Bey-Dih Chang, Lombard, IL (US); Igor B. Roninson, Wilmette, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/449,589

(22) Filed: Nov. 29, 1999

Related U.S. Application Data
(60) Provisional application No. 60/128,676, filed on Apr. 9, 1999.

(51) Int. Cl.[7] .................................................. C12Q 1/02
(52) U.S. Cl. ............................ 435/29; 435/4; 435/7.21
(58) Field of Search .......................... 435/4, 6, 7.1, 7.2, 435/7.21, 29

(56) References Cited

U.S. PATENT DOCUMENTS

| | | | | |
|---|---|---|---|---|
| 5,424,400 A | * | 6/1995 | Smith | 530/350 |
| 5,654,168 A | | 8/1997 | Bujard et al. | 435/69.1 |
| 5,744,300 A | * | 4/1998 | Linskens et al. | 435/6 |
| 5,807,692 A | | 9/1998 | Kinzler et al. | 435/7.21 |
| 5,851,796 A | | 12/1998 | Schatz | 435/69.1 |
| 5,968,773 A | | 10/1999 | Heddle et al. | 435/69.1 |

OTHER PUBLICATIONS

Niculescu et al. Effects of p21 cip1/Waf1 at both the G1/s and the G2/M cell cycle transitions: pRb is a critical determinant in blocking DNA replication and in preventing endoreduplication. Molecular and Cellular Biology. 1998, vol. 18, pp. 629–643.*
Vogt et al. Independent induction of senescence by p16INK4a and p21CIP1 in spontaneously immortalized human fibroblasts. Cell Growth and Differentiation. 1998. vol. 9, pp. 139–146.*
Adler et al., 1991, Proc. Natl. Acad. Sci. 88:16–20.
Akahani et al., 1997, Cancer Res. 57:5272–5276.
Albini et al., 1988, Coll. Relat. Res. 8:23–37.
Alcorta et al., 1996, Proc. Natl. Acad. Sci. USA 93:13742–13747.
Asada et al., 1999, EMBO J. 18:1223–1234.
Bates et al., 1998 Oncogene 17:1691–1703.
Berstein et al., 1990, Brain Res. Bull 24:43–549.
Bissonette & Hunting, 1998, Oncogene 16:3461–3469.
Bradham et al., 1991, J. Cell. Biol. 114:1285–1294.
Brown et al., 1997, Science 277:831–834.
Bunz et al., 1998, Science 282:1497–1501.
Campisi et al., 1998, J. Investig. Dermatol. Symp. Proc. 3:1–5.
Cerinic et al., 1998, Life Sci. 63:441–453.
Chan et al., 1999, J. Cell. Biol. 146:941–954.
Chang et al., 1999, Cancer Res. 59:3761–3767.
Chang et al., 1999, Oncogene 18:4808–4818.
Chevalier, 1993, Semin. Arthritis Rheum. 22:307–318.
Crisofalo & Pignolo, 1996, Exp. Gerontol. 31: 111–123.
Cristofalo & Kabakijan, 1975, Mech. Aging Dev. 4:19–28.
de Toledo et al., 1998, Cell Growth Differ. 9:887–896.
Deng et al., 1995, Cell 82:675–684.
deWinter et al., 1998, Nat. Genet 20:281–283.
Di Cunto et al., 1998, Science 280:1069–1072.
Diatchenko et al., 1996, Proc. Natl. Acad. Sci. USA 93:6025–6030.
DiLeonardo et al., 1994, Genes Develop. 8:2540–2551.
Dimri et al., 1995, Proc. Natl. Acad. Sci. USA 92:9363–9367.
diPaolo et al., 1992, Exp. Cell Res. 201:500–505.
Doggett et al., 1992, Mech. Aging Dev. 65:239–255.
Dudek & Johnson, 1994, Brain Res. 651:129–133.
el–Deiry et al., 1995, Cancer Res. 55:2910–2919.
Fang et al., 1999, Oncogene 18:2789–2797.
Gartel et al., 1999, Exp. Cell Res. 246:280–289.
Gerring et al., 1990, EMBO J. 9:4347–4358.
Glover et al., 1998, Genes Develop. 12:3777–3787.
Gorospe et al., 1997, Oncogene 14:929–935.
Gray et al., 1997, Nature Genet. 17:100–103.
Grilli et al., 1996, J. Biol. Chem. 271:15002–15007.
Hall & Peters, 1996, Adv. Cancer Res. 68:67–108.
Harper et al., 1993, Cell 75:805–816.
Hashimoto et al., 1997, Biochem. Biophys Res. Commun. 240:88–92.
Hasimoto et al., 1987, Thromb. Res. 46:625–633.
Hayflick & Moorhead, 1961, Exp. Cell Res. 25:585–621.
Hiraiwa et al., 1997, Proc. Nat. Acad. Sci. USA 94:4778–4781.
Hixon et al., 1998, Mol. Cell. Biol. 18:6224–37.
Horan & Slezak, 1989, Nature 340:167–168.
Howie et al., 1985, J. Pathol. 145:307–314.
Inohara et al., 1998, Exp Cell Res. 245:294–302.
Jensen & Whitehead, 1998, Biochem J. 334:489–503.
Jiang et al., 1998, Mol. Cell 2:877–885.
Jones et al., 1997, Mol. Cell. Biol. 17:6970–6981.
Jordan et al., 1996, Cancer Res. 56:816–825.
Kearsey et al., 1995, Oncogene 11:1675–1683.
Kimura et al., 1997, J. Biol. Chem. 272:13766–13771.
Kodama et al., 1995, Exp. Cell. Res. 219:82–86.
Komarova et al., 1998, Oncogene 17:1089–1096.
Kumazaki et al., 1998, Mech. Aging Dev. 101–91–99.

(List continued on next page.)

Primary Examiner—James Ketter
Assistant Examiner—Bronwer M. Loeb
(74) Attorney, Agent, or Firm—McDonnell Boehnen Hulbert & Berghoff

(57) ABSTRACT

This invention provides methods and reagents for identifying genes involved in cell cycle progression, growth promotion, modulation of apoptosis, cellular senescence and aging, and methods for identifying compounds that inhibit or potentiate cellular senescence.

15 Claims, 9 Drawing Sheets

OTHER PUBLICATIONS

Li and Benezra, 1996, Science 274:246–248.
Loria et al., 1998, Eur. J. Endocrinol. 139:487–492.
Losada et al, 1998, Genes Develop. 12:1986–1997.
Lowe et al., 1994, Proc. Natl. Acad. Sci USA 91:2026–2030.
Lowe et al., 1994, Science 266:807–810.
Lu et al., 1998, Oncogene 16:705–712.
Madaule et al., 1998, Nature 394:491–494.
Manna et al., 1998, J. Biol. Chem. 273:13245–13254.
Mathur et al., 1994, Biochem. Mol. Biol. Int. 34:1063–1071.
McDonnell et al., 1998, Curr. Biol. 8:351–354.
McKay et al., 1996, Genomics 36:305–315.
Mirza et al., 1997, Amer. J. Physiol 272:G281–G288.
Mosca et al., 1992, Mol. Cell. Biol. 12:4375–4383.
Nachtigal et al., 1998, Am. J. Pathol. 152:1199–1208.
Nakanishi et al., 1995, EMBO J. 14:555–563.
Nevins, 1998, Cell Growth Differ. 9:585–593.
Nikiforov et al., 1996, Oncogene 13:1709–1719 tops of pages not visible—considered abstract only.
Noda et al., 1994, Exp. Cell. Res. 211:90–98.
Noonan et al., 1990, Proc. Natl. Acad. Sci. USA 87:7160–7164.
Oemar et al., 1997, Circulation 95:831–839.
Ogomori et al., 1988, J. Gerontol. 43:B157–B162.
Pan et al., 1995, J. Biol. Chem. 270:22008–22016.
Pantoja et al., 1999, Oncogene 18:4974–4982.
Park et al., 1999, J. Geronotol. A. Biol. Sci. 54:B78–B83.
Perkins et al., 1988, Science 275:523–527.
Perry et al., 1992, Mutat. Res. 276:189–197.
Prabhu et al., 1996, Clin Cancer Res. 2:1221–1229.
Robles & Adami, 1998, Oncogene 16:1113–1123.
Rosenthal & Franklin, 1975, J. Clin. Invest. 55:746–753.
Sakurai et al., 1994, J. Biol. Chem. 269:14118–14122.
Seki et al., 1998, Arthritis Rheum 41:1356–1364.
Serrano et al., 1997, Cell 88:593–602.
Shim et al., 1996, Nature 381:804–807.
Shoyab et al., 1990, Proc. Natl. Acad. Sci. USA 87:7912–7916.
Sims et al., 1998, Neurobiol. Aging 19:385–391.
Singhal et al., 1997, J. Investig. Med. 45:567–575.
Snowden & Perkins, 1988, Biochem. Pharmacol. 55:1947–1954.
Stein et al., 1999, Mol. Cell. Biol. 19:2109–2117.
Sugrue et al., 1997, Proc. Natl. Acad. Sci. USA 94:9648–9653.
Suzuki et al., 1998, FEBS Lett. 437:112–116.
Terada et al., 1998, EMBO J. 17:667–676.
Tsao et al., J. Virol 73:4983–4990 1999.
Uhrbom et al., 1997, Oncogene 15:505–514.
Umar et al., 1996, Cell 87:65–73.
Veerhuis et al., 1995, Virchows Arch. 426:603–610.
Waldman et al., 1995, Cancer Res. 55:5187–5190.
Xu et al., 1997, Oncogene 15:2589–2596.
Zhu et al., 1997, Exp. Cell. Res. 234:293–299.

Gartel et al. 1996, Exp. Cell Res. 227:171–181.
Nakanishi et al., "The C–terminal region of p21 SDI1/WAF1/CIP1 is involved in proliferating cell nuclear antigen binding but does not appear to be required for growth inhibition", The Journal of Biological Chemistry, vol. 270, No. 29, Jul. 21, 1995 pp. 17060–17063.
Nakanishi et al., "Identification of the Active region of the DNA synthesis inhibitory gene p21 Sdi1/CIP1/WAF1", The EMBO Journal, vol. 14, No. 3, 1995, pp. 555–563.
Chang et al., "Effects of p21 Waf1/Cip1/Sdi1 on cellular gene expression: Implications for carcinogenesis, senescence, and age–related diseases" Proceedings of the National Academy of Sciences of the United States of America, vol 97, No. 8, Apr. 11, 2000, pp. 4291–4296.
Chang et al. "p21 Waf1/Cip1/Sdi1–induced growth arrest is associated with depletion of mitosis–control proteins and leads to abnormal mitosis and endoreduplication in recovering cells", Oncogene, vol. 19, No. 17, Apr. 20, 2000, pp. 2165–2170.
Hsiao et al., "Functional expression of human p21 WAF1/CIP1 gene in rat glioma cells suppresses tumor growth in vivo and induces radiosensitivity", Biochemical and Biophysical Research Communications, vol. 233, 1997, pp. 329–335.
Vogt et al., "Independent induction of senescence by p16INK4a and p21CIP1 in spontaneously immortalized human fibroblasts", Cell Growth and Differentiation, vol. 9, No. 2, Feb. 1998, pp. 139–146.
Zeng et al., Regulation of p21(WAF1/CIP1) expression by p53–independent pathways, Oncogene, (1996) 12/7 (1557–1564).
Afshari et al., "A Role for a p21–E2F interaction during senescence arrest of normal human fibroblasts", Cell Growth and Differentiation, (1996) 7/8 (979–988).
Johnson et al., "Evidence for p53–independent pathway for upregulatiion of SDI1/CIP1/WAF1/p21 RNA in human cells", Molecular Carcinogenesis, vol. 11, No. 2, Oct. 1994, pp. 59–64.
Chang et al., "Role of p53 and p21 (waf1/cip1) in senescence–like terminal proliferation arrest induced in human tumor cells by chemotherapeutic drugs", Oncogene, Aug. 26, 1999, pp. 4808–4818.
Chang et al., "Transient overexpression of p21 WAF1/CIP1 induces cell death and features of senescence in a human fibrosarcoma line" Proceeding of the Americal Association for Cancer Research Annual Meeting, vol. 40, Mar. 1999, pp. 94–95.
Xiao et al., "Sodium butyrate induces NIH3T3 cells to senescence–like state and enhances promoter activity of p 21 waf/CIP1 in p53–independent manner", Biochemical and Biophysical Research Communications, vol. 237, 1997, pp. 457–460.

* cited by examiner

Figure 1. IPTG-regulated retroviral vector LNp21CO3

Release after 1-day IPTG treatment

C, control untreated cells; I, IPTG-treated,
Q, serum-starved (quiescent) cells

REAGENTS AND METHODS FOR IDENTIFYING AND MODULATING EXPRESSION OF GENES REGULATED BY P21

BACKGROUND OF THE INVENTION

This is a continuation of U.S. patent application Ser. No. 60/128,676, filed Apr. 9, 1999, the disclosure of which is explicitly incorporated by reference herein.

This application was supported by a Public Service grant from the National Cancer Institute, grant number R01 CA62099. The U.S. government may have certain rights to this invention.

FIELD OF THE INVENTION

This invention is related to cellular senescence and changes in cellular gene expression that accompany senescence. In particular, the invention is related to the identification of genes the expression of which is modulated by a cellular gene product, p21, induced in cells at the onset of senescence. More specifically, the invention provides markers of cellular senescence that are genes whose expression in induced or repressed by p21. The invention provides methods for identifying compounds that inhibit or potentiate cellular senescence by detecting inhibition of repression or induction of these marker genes. Also provided are reagents that are recombinant mammalian cells containing a recombinant expression construct encoding p21 that is experimentally-inducible, and recombinant mammalian cells containing a recombinant expression construct that expresses a reporter gene under the transcriptional control of a promoter for a gene that is regulated by p21.

SUMMARY OF THE RELATED ART $p21^{WAF1/CIP1/SDI1}$ is an important mediator of growth arrest and senescence in mammalian cells. p21 has been independently identified by several groups as a protein that binds and inhibits cyclin-dependent kinases (CDK) (Harper et al., 1993, Cell 75: 805–816), as a gene upregulated by wild-type p53 (el-Deiry et al., 1993, Cancer Res. 55: 2910–2919), and as a growth-inhibitory gene overexpressed in senescent fibroblasts (Noda et al., 1994, Exp. Cell. Res. 211: 90–98). Because of its pivotal role in p53-regulated growth arrest, p21 is usually regarded as a tumor suppressor. Nevertheless, p21 mutations in human cancer are rare (Hall & Peters, 1996, Adv. Cancer Res. 68: 67–108), and p21 knockout mice develop normally and do not show an increased rate of tumorigenesis (Deng et al., 1995, Cell 82: 675–684).

Cellular levels of p21 are increased in response to a variety of stimuli, including DNA-damaging and differentiating agents. Some of these responses are mediated through transcriptional activation of the p21 gene by p53, but p21 is also regulated by a variety of p53-independent factors (reviewed in Gartel & Tyner, 1999, Exp. Cell Res. 227: 171–181). Increased p21 expression leads to cell growth arrest (Noda et al., 1994, ibid.), which occurs in both G1 and G2 (Niculescu et al., 1998, Mol. Cell. Biol. 18: 629–643) and is accompanied by the development of morphologic and phenotypic markers of senescence (Vogt et al., 1998, Cell Growth Differ. 9: 139–146; McConnell et al., 1998, Curr. Biol. 8: 351–354; Bates et al., 1998, Oncogene 17: 1691–1703; Fang et al., 1999, Oncogene 18: 2789–2797).

Transient induction of p21 mediates different forms of damage-induced growth arrest, including transient arrest that allows cell to repair DNA damage, as well as permanent growth arrest (also termed "accelerated senescence"), which is induced in normal fibroblasts (DiLeonardo et al., 1994, Genes Develop. 8: 2540–2551; Robles & Adami, 1998, Oncogene 16: 1113–1123) and tumor cells (Chang et al., 1999, Cancer Res. 59: 3761–3767) by DNA damage or introduction of oncogenic RAS (Serrano et al., 1997, Cell 88: 593–602). A surge of p21 expression also coincides with the onset of terminal growth arrest during replicative senescence of aging fibroblasts (Noda et al., 1994, ibid.; Alcorta et al., 1996, Proc. Natl. Acad. Sci USA 93:13742–13747; Stein et al., 1999, Mol. Cell. Biol. 19: 2109–2117) and terminal differentiation of postmitotic cells (El-Deiry et al., 1995, ibid.; Gartel et al., 1996, Exp. Cell Res. 246: 280–289). Analysis of cells that cannot express p21 (p21−/− homozygotes) demonstrated the requirement of p21 in transient G1 and G2 arrest (Deng et al., 1995, ibid.; Waldman et al., 1995, Cancer Res. 55: 5187–5190; Bunz et al., 1998, Science 282: 1497–1501), in replicative senescence of normal fibroblasts (Brown et al., 1997, Science 277: 831–834), and in accelerated senescence of tumor cells (Chang et al., 1999, Oncogene 18: 4808–4818).

While p21 is not a transcription factor per se, it has indirect effects on gene expression that may play a role in its cellular functions. The best-known biochemical function of p21 is the inhibition of CDK complexes that regulate transitions between different phases of the cell cycle (reviewed in Cartel & Tyner, 1998, "The growth-regulatory role of p21 (WAF1/CIP1)," in Inhibitors of Cell Growth, Progess in Molecular and Subcellular Biology, Vol. 20 (A. Macieir-Coelho, ed.), Springer-Verlag: Berlin Heidelberg, pp. 43–71.). One of the consequences of CDK inhibition is dephosphorylation of Rb, which in turn inhibits E2F transcription factors that regulate many genes involved in DNA replication and cell cycle progression (Nevins, 1998, Cell Growth Differ. 9: 585–593). A comparison of p21-expressing cells (p21+/+) and p21-nonexpressing cells (p21−/−) has implicated p21 in radiation-induced inhibition of several E2F-regulated cellular genes (de Toledo et al., 1998, Cell Growth Differ. 9: 887–896). Another result of CDK inhibition by p21 is stimulation of transcription cofactor p300 that augments NFκB (Perkins et al., 1988, Science 275: 523–527). Activation of histone acetyltransferase p300, that enhances many inducible transcription factors, may have a pleiotropic effect on gene expression (Snowden & Perkins, 1988, Biochem. Pharmacol. 55: 1947–1954). p21 may also affect gene expression through its interactions with proteins other than CDK. For example, p21 has been found to inhibit the expression of keratinocyte differentiation markers; this effect was dependent on the C-terminal portion of p21, which is not required for CDK inhibition but is known to bind the proliferating cell nuclear antigen (Di Cunto et al., 1998, Science 280: 1069–1072). p21 was also reported to bind JNK kinases (Shim et al., 1996, Nature 381: 804–807), apoptosis signal-regulating kinase 1 (Asada et al., 1999, EMBO J. 18: 1223–1234), and Gadd45 (Kearsey et al., 1995, Oncogene 11: 1675–1683); these interactions may affect the expression of genes regulated by the corresponding pathways.

There remains a need in this art to identify genes whose expression is modulated by induction of p21 gene expression. There is also a need in this art to develop targets for assessing the effects of compounds on cellular senescence, carcinogenesis and age-related diseases.

SUMMARY OF THE INVENTION

This invention provides reagents and methods for identifying genes whose expression is modulated by induction of p21 gene expression. The invention also provides reagents and methods for identifying compounds that inhibit or potentiate the effects of p21 on cellular gene expression, as a first step in rational drug design for preventing cellular senescence, carcinogenesis and age-related diseases or for increasing the efficacy of anticancer therapies.

In a first aspect, the invention provides a mammalian cell containing an inducible p21 gene. In preferred embodiments, the mammalian cell is a recombinant mammalian cell comprising a recombinant expression construct encoding an inducible p21 gene. More preferably, the construct comprises a nucleotide sequence encoding p21, most preferably human p21, under the transcriptional control of an inducible promoter. In alternative embodiments, the construct comprises a nucleotide sequence encoding the amino-terminal portion of p21 comprising the CDK binding domain, more preferably comprising amino acids 1 through 78 of the p21 amino acid sequence. In more preferred embodiments, the inducible promoter can be induced by contacting the cells with an inducing agent, most preferably a physiologically-neutral inducing agent, that induces transcription from the inducible promoter or by removing an agent that inhibits transcription from such promoter. In a preferred embodiment, the mammalian cell is a fibrosarcoma cell.

In another embodiment of the first aspect of the invention are provided recombinant mammalian cells comprising a recombinant expression construct in which a reporter gene is under the transcriptional control of a promoter derived from a cellular gene whose expression is modulated by p21. In a preferred embodiment, the promoter is derived from a cellular gene whose expression is repressed by p21. In these embodiments, the promoter is most preferably derived from a gene identified in Table I. Most preferably, the promoter is derived from ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, Rad54, exonuclease HEX1/RAD2, or citron kinase. In other preferred embodiments, the promoter is derived from a cellular gene whose expression is induced by p21. In these embodiments, the promoter is most preferably derived from a gene identified in Table II. Most preferably, the promoter is derived from serum amyloid A, complement C3, connective tissue growth factor, integrin β-3, activin A, natural killer cell protein 4, prosaposin, Mac2 binding protein, galectin-3, superoxide dismutase 2, or cathepsin B. Preferred reporter genes comprising the recombinant expression constructs of the invention include firefly luciferase, chloramphenicol acetyltransferase, beta-galactosidase, green fluorescent protein, or alkaline phosphatase.

In additional preferred embodiments, the invention provides a mammalian cell comprising a first recombinant expression construct encoding a reporter gene under the transcriptional control of a promoter for a mammalian gene whose expression is modulated by p21, and a second recombinant expression construct encoding a mammalian p21 gene, wherein expression of p21 is experimentally-induced in the mammalian cell thereby. In preferred embodiments, the recombinant expression construct encoding a mammalian p21 gene is under the transcriptional control of an inducible heterologous promoter, wherein expression of p21 from the recombinant expression construct is mediated by contacting the recombinant cell with an inducing agent that induces transcription from the inducible promoter or by removing an agent that inhibits transcription from such promoter. Preferably, the construct comprises a nucleotide sequence encoding p21, most preferably human p21. In alternative embodiments, the construct comprises a nucleotide sequence encoding the amino-terminal portion of p21 comprising the CDK binding domain, more preferably comprising amino acids 1 through 78 of the p21 amino acid sequence. In a preferred embodiment, the promoter is derived from a cellular gene whose expression is repressed by p21. In these embodiments, the promoter is most preferably derived from a gene identified in Table I. In other preferred embodiments, the promoter is derived from a cellular gene whose expression is induced by p21. In these embodiments, the promoter is most preferably derived from a gene identified in Table II. Preferred reporter genes comprising the recombinant expression constructs of the invention include firefly luciferase, chloramphenicol acetyltransferase, beta-galactosidase, green fluorescent protein, or alkaline phosphatase. In a preferred embodiment, the mammalian cell is a fibrosarcoma cell.

In a second aspect, the invention provides a conditioned cell culture medium wherein the medium is conditioned by cells expressing p21. A method for producing said conditioned medium, comprising the step of culturing p21-expressing cells in a mammalian cell culture medium is also provided.

In a third aspect, the invention provides methods for identifying compounds that inhibit p21-mediated modulation of cellular gene expression. These methods comprise the steps of inducing or otherwise producing p21 in a mammalian cell; assaying the cell in the presence of the compound for changes in expression of cellular genes whose expression is modulated by p2l; and identifying compounds that inhibit p21-mediated modulation of cellular gene expression if expression of the cellular genes is changed to a lesser extent in the presence of the compound than in the absence of the compound. In preferred embodiments, the cellular genes are repressed by p21, and inhibitors are detected by detecting expression of the genes at levels greater than those detected when p21 is expressed in the absence of the compound. In preferred embodiments, the genes are identified in Table I. In alternative preferred embodiments, the cellular genes are induced by p21, and inhibitors are detected by detecting expression of the genes at levels less than those detected when p21 is expressed in the absence of the compound. In preferred embodiments, the genes are identified in Table II. In further alternative embodiments, the method is performed using a recombinant mammalian cell comprising a reporter gene under the transcriptional control of a promoter derived from a gene whose expression is modulated by p21. In these embodiments using constructs comprising promoters derived from genes repressed by p21, the reporter gene product is produced at greater levels in the presence than in the absence of the compound when the compound is an inhibitor of p21 gene expression modulation. In these embodiments, the promoter is most preferably derived from a gene identified in Table I. Most preferably, the promoter is derived from ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, Rad54, exonuclease HEX1/RAD2, or citron kinase. When using constructs comprising promoters derived from genes induced by p21, the reporter gene product is produced at lesser levels in the presence than the absence of the compound when the compound is an inhibitor of p21 gene expression modulation. In these embodiments, the promoter is most preferably derived from a gene identified in Table II. Most preferably, the promoter is derived from serum amyloid A, complement C3, connective tissue growth factor, integrin β-3, activin A, natural killer cell protein 4, prosaposin, Mac2 binding protein, galectin-3, superoxide dismutase 2, or cathepsin B. Preferred reporter genes comprising the recombinant expression constructs of the invention include firefly luciferase, chloramphenicol acetyltransferase, beta-galactosidase, green fluorescent protein, or alkaline phosphatase. In other preferred embodiments, the cell comprises a first recombinant expression construct encoding a reporter gene under the transcriptional control of a promoter for a mammalian gene whose expression is modulated by p21, and a second recombinant expression construct encoding a mammalian p21 gene, wherein expression of p21 is experimentally-induced in the mammalian cell thereby. The product of the reporter gene or the endogenous gene that is induced or repressed by p21 is detected using an immunological reagent, by assaying for an activity of the gene product, or by hybridization to a complementary nucleic acid.

In a fourth aspect, the invention provides methods for identifying compounds that inhibit senescence in a mammalian cell. These methods comprise the steps of treating the mammalian cell in the presence of the compound with an agent or culturing the mammalian cell under conditions that induce senescence; assaying the mammalian cell for repression or induction of genes that are repressed or induced by p21 gene expression; and identifying the compound as an inhibitor of senescence if genes that are repressed by p21 are not repressed, or genes that are induced by p21 are not induced, in the presence of the compound. In preferred embodiments, the cellular genes are repressed by p21, and senescence inhibitors are identified by detecting expression of the genes at levels greater than those detected when p21 is expressed in the absence of the compound. In preferred embodiments, the genes are identified in Table I. In alternative preferred embodiments, the cellular genes are induced by p21, and senescence inhibitors are detected by detecting expression of the genes at levels less than those detected when p21 is expressed in the absence of the compound. In preferred embodiments, the genes are identified in Table II. In further alternative embodiments, the method is performed using a recombinant mammalian cell comprising a reporter gene under the transcriptional control of a promoter derived from a gene whose expression is modulated by p21. In these embodiments, production of the product of the reporter gene at greater levels in the presence than in the absence of the compound when using constructs comprising promoters derived from genes repressed by p21, or at lesser levels in the presence than the absence of the compound when using constructs comprising promoter derived from genes induced by p21, is detected when the compound is an inhibitor of senescence. The promoters are preferably derived from genes identified in Table I (for genes repressed by p21) or Table II (for genes induced by p21). For p21-repressed IS genes, the promoter is most preferably derived from ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, Rad54, exonuclease HEX1/RAD2, or citron kinase. For p21-induced genes, the promoter most preferably is derived from serum amyloid A, complement C3, connective tissue growth factor, integrin β-3, activin A, natural killer cell protein 4, prosaposin, Mac2 binding protein, galectin-3, superoxide dismutase 2, or cathepsin B. In other preferred embodiments, the cell comprises a first recombinant expression construct encoding a reporter gene under the transcriptional control of a promoter for a mammalian gene whose expression is modulated by p21, and a second recombinant expression construct encoding a mammalian p21 gene, wherein expression of p21 is experimentally-induced in the mammalian cell thereby. The product of the reporter gene or the endogenous gene that is induced or repressed by p21 is detected using an immunological reagent, by assaying for an activity of the gene product, or by hybridization to a complementary nucleic acid.

In a fifth aspect, the invention provides methods for inhibiting cellular senescence, age-related diseases or age-associated gene products, the method comprising the steps of contacting the cell with a compound that inhibits senescence as determined using the methods provided in the aforesaid aspects of the invention.

In a sixth aspect, the invention provides methods for identifying compounds that potentiate senescence in a mammalian cell. These methods comprise the steps of inducing p21 in the mammalian cell in the presence and absence of the compound; assaying the mammalian tumor cell for repression or induction of genes that are repressed or induced by p21 gene expression; and identifying the compound as a potentiator of senescence if genes that are repressed by p21 are repressed to a greater extent, or genes that are induced by p21 are induced to a greater extent, in the presence of the compound. In preferred embodiments, the cellular genes are repressed by p21, and potentiators are detected by detecting expression of the cellular gene at levels less than those detected when p21 is expressed in the absence of the compound. In preferred embodiments, the genes are identified in Table I. In alternative preferred embodiments, the cellular genes are induced by p21, and potentiators are detected by detecting expression of the cellular gene at levels greater than those detected when p21 is expressed in the absence of the compound. In preferred embodiments, the genes are identified in Table II. In further alternative embodiments, the method is performed using recombinant mammalian cells comprising a reporter gene under the transcriptional control of a promoter derived from a gene whose expression is modulated by p21, wherein the cells comprise constructs having the reporter gene under the transcriptional control of promoters from genes whose expression is modulated by p21. In these embodiments, production of the product of the reporter gene at lower levels in the presence than in the absence of the compound when using constructs comprising promoters derived from genes repressed by p21, or at greater levels in the presence than the absence of the compound when using constructs comprising promoter derived from genes induced by p21, is detected when the compound is a potentiator of senescence. In preferred embodiments, the promoters are derived from genes whose expression is repressed by p21, most preferably genes identified in Table I. Most preferably, the promoter is derived from ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, Rad54, exonuclease HEX1/RAD2, or citron kinase. In alternative preferred embodiments, the promoters are derived from genes whose expression is induced by p21, most preferably genes identified in Table II. Most preferably, the promoter is derived from serum amyloid A, complement C3, connective tissue growth factor, integrin β-3, activin A, natural killer cell protein 4, prosaposin, Mac2 binding protein, galectin-3, superoxide dismutase 2, or cathepsin B. In other preferred embodiments, the cell comprises a first recombinant expression construct encoding a reporter gene under the transcriptional control of a promoter for a mammalian gene whose expression is modulated by p21, and a second recombinant expression construct encoding a mammalian p21 gene, wherein expression of p21 is experimentally-induced in the mammalian cell thereby. The product of the reporter gene or the endogenous gene that is induced or repressed by p21 is detected using an immunological reagent, by assaying for an activity of the gene product, or by hybridization to a complementary nucleic acid.

In a seventh aspect, the invention provides methods for promoting or potentiating cellular senescence in tumor cells, hyperplastic cells or any cell type that is pathological or disease-causing due to excessive proliferation, the method comprising the steps of contacting the cell with a compound that potentiates senescence as determined using the methods provided in the aforesaid aspect of the invention.

In a eighth aspect, the invention provides compounds that are identified using any of the methods of the invention as disclosed herein.

In a ninth aspect, the invention provides methods for obtaining a plurality of nucleic acid species enriched for genes involved in cell cycle progression. These methods comprise the steps of inducing the expression of p21 in a mammalian cell; obtaining cellular mRNA from a mammalian cell before p21 induction and after p21 is induced and cell growth is stopped; and obtaining the plurality of nucleic acid species enriched for genes involved in cell cycle progression. In a preferred embodiment, the plurality of nucleic acid species enriched for cell cycle progression genes is obtained by subtractive hybridization methods known in the art, whereby nucleic acid species underrepresented in cells expressing p21 are selectively enriched.

In a tenth aspect, the invention provides methods for obtaining a plurality of nucleic acid species enriched for genes that encode secreted proteins with paracrine functions and proteins involved in senescence and age-related diseases. These methods comprise the steps of inducing expression of p21 in a mammalian cell; obtaining cellular mRNA from a mammalian cell before and after p21 is induced; and obtaining the plurality of nucleic acid species enriched for genes whose expression is increased in the cell after p21 is induced. In preferred embodiments, the paracrine functions of the proteins are mitogenic and anti-apoptotic effects. In a preferred embodiment, the plurality of nucleic acid species enriched for genes that encode secreted proteins with paracrine functions and proteins involved in senescence and age-related diseases is obtained by subtractive hybridization methods known in the art, whereby nucleic acid species overrepresented in cells expressing p21 are selectively enriched.

In an eleventh aspect, the invention provides a method for identifying genes that are markers of cellular senescence, the method comprising the steps of inducing senescence by producing p21 expression in a first population of mammalian cells and inducing quiescence in a second population of mammalian cells; obtaining mRNA from each population of cells; comparing the pattern of gene expression in cells before and after production or p21 in the cells with the pattern of gene expression in cells before and after the cells became quiescent; comparing the plurality of genes strongly induced in the cells after p21 is produced with the plurality of genes strongly induced in quiescent cells; and identifying the genes strongly induced in cells producing p21 that are not strongly induced in quiescent cells.

In a twelfth aspect, the invention provides methods for detecting senescence in a mammalian cell. These methods comprise the step of detecting expression of a gene that is a marker for senescence. In preferred embodiments, preferred markers of senescence include connective tissue growth factor (CTGF), serum amyloid A, integrin $\beta$-3, activin A, natural killer cell protein 4, Mac2 binding protein, or tissue transglutaminase.

In a thirteenth aspect, the invention provides methods for identifying compounds that promote induction of senescence in a mammalian cell. These methods comprise the steps of treating the mammalian cell with an agent or culturing the mammalian cell under conditions that induce senescence in the presence of the compound; assaying the mammalian tumor cell for repression or induction of genes that are repressed or induced by p21 gene expression; and identifying the compound as a potentiator of senescence if genes that are repressed by p21 are further repressed, i.e., to a greater extent, or genes that are induced by p21 are further induced, i.e., to a greater extent, in the presence of the compound. In preferred embodiments, the cellular genes are repressed by p21, and compounds that promote induction of senescence are detected by detecting expression of the cellular gene at levels less than those detected when p21 is expressed in the absence of the compound. In preferred embodiments, the genes are identified in Table I. In alternative preferred embodiments, the cellular genes are induced by p21, and compounds that promote induction of senescence are detected by detecting expression of the cellular gene at levels greater than those detected when p21 is expressed in the absence of the compound. In preferred embodiments, the genes are identified in Table II. In further alternative embodiments, the method is performed using recombinant mammalian cells comprising a reporter gene under the transcriptional control of a promoter derived from a gene whose expression is modulated by p21, wherein the cells comprise constructs having the reporter gene under the transcriptional control of promoters from genes whose expression is modulated by p21. In these embodiments, production of the product of the reporter gene at lower levels in the presence than in the absence of the compound when using constructs comprising promoters derived from genes repressed by p21, or at greater levels in the presence than the absence of the compound when using constructs comprising promoter derived from genes induced by p21, is detected when the compound promotes induction of senescence. In preferred embodiments, the promoters are derived from genes whose expression is repressed by p21, most preferably genes identified in Table I. Most preferably, the promoter is derived from ORC1, PRC1, XRCC9, CDC2, cyclin B1, AIK1, CENP-A, CENP-F, MAD2, BUBR1, MCAK, HSET, CHL1, thymopoietin $\alpha$, MPP2, MPP5, CDC47/MCM7, CDC21/MCM4, DNA ligase I, DNA polymerase $\alpha$, Rad54, exonuclease HEX1/RAD2, or citron kinase. In alternative preferred embodiments, the promoters are derived from genes whose expression is induced by p21, most preferably genes identified in Table II. Most preferably, the promoter is derived from serum amyloid A, complement C3, connective tissue growth factor, integrin $\beta$-3, activin A, natural killer cell protein 4, prosaposin, Mac2 binding protein, galectin-3, superoxide dismutase 2, or cathepsin B. In other preferred embodiments, the cell comprises a first recombinant expression construct encoding a reporter gene under the transcriptional control of a promoter for a mammalian gene whose expression is modulated by p21, and a second recombinant expression construct encoding a mammalian p21 gene, wherein expression of p21 is experimentally-induced in the mammalian cell thereby. The product of the reporter gene or the endogenous gene that is induced or repressed by p21 is detected using an immunological reagent, by assaying for an activity of the gene product, or by hybridization to a complementary nucleic acid.

In a fourteenth aspect, the invention provides methods for identifying compounds that induce senescence in a mammalian cell. These methods comprise the steps of assaying a mammalian cell in the presence and absence of the compound for repression or induction of genes that are repressed or induced by p21 gene expression; and identifying compounds that induce senescence if genes that are repressed by p21 are repressed, or genes that are induced by p21 are induced, in the presence of the compound. In preferred embodiments, the cellular genes are repressed by p21, and compounds that induce senescence are detected by detecting expression of the cellular gene at levels less than those detected in the absence of the compound. In preferred embodiments, the genes are identified in Table I. In alternative preferred embodiments, the cellular genes are induced by p21, and compounds that induce senescence are detected by detecting expression of the cellular gene at levels greater than those detected in the absence of the compound. In preferred embodiments, the genes are identified in Table II. In further alternative embodiments, the method is performed using recombinant mammalian cells comprising a reporter gene under the transcriptional control of a promoter derived from a gene whose expression is modulated by p21, wherein the cells comprise constructs having the reporter gene under the transcriptional control of promoters from genes whose expression is modulated by p21. In these embodiments, production of the product of the reporter gene at lower levels in the presence than in the absence of the compound when using constructs comprising promoters derived from genes repressed by p21, or at greater levels in the presence than the absence of the compound when using constructs comprising promoter derived from genes induced by p21, is detected when the compound induces senescence. In preferred embodiments, the promoters are derived from genes whose expression is repressed by p21, most preferably genes identified in Table I. Most preferably, the promoter is derived from ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, Rad54, exonuclease HEX1/RAD2, or citron kinase. In alternative preferred embodiments, the promoters are derived from genes whose expression is induced by p21, most preferably genes identified in Table II. Most preferably, the promoter is derived from serum amyloid A, complement C3, connective tissue growth factor, integrin β-3, activin A, natural killer cell protein 4, prosaposin, Mac2 binding protein, galectin-3, superoxide dismutase 2, or cathepsin B. The product of the reporter gene or the endogenous gene that is induced or repressed by p21 is detected using an immunological reagent, by assaying for an activity of the gene product, or by hybridization to a complementary nucleic acid.

Specific preferred embodiments of the present invention will become evident from the following more detailed description of certain preferred embodiments and the claims.

DETAILED DESCRIPTION OF THE PREFERRED EMBODIMENTS

Figure 1:
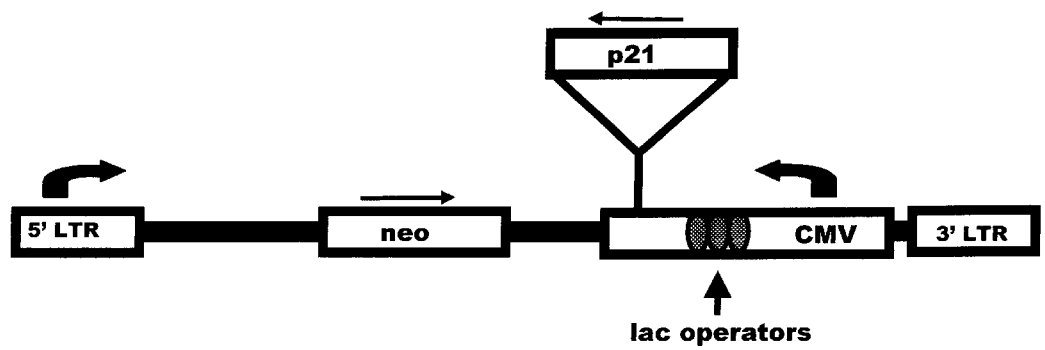
FIG. 1 is a schematic diagram of the IPTG-regulated retroviral vector LNp21CO3 used to produce the human HT1080 fibrosarcoma cell line variant p21-9.

This invention provides reagents and methods for identifying genes involved in mediating p21-induced cellular senescence, and compounds capable of inhibiting or potentiating senescence or quiescence in mammalian cells.

For the purposes of this invention, reference to "a cell" or "cells" is intended to be equivalent, and particularly encompasses in vitro cultures of mammalian cells grown and maintained as known in the art.

For the purposes of this invention, reference to "cellular genes" in the plural is intended to encompass a single gene as well as two or more genes. It will also be understood by those with skill in the art that effects of modulation of cellular gene expression, or reporter constructs under the transcriptional control of promoters derived from cellular genes, can be detected in a first gene and then the effect replicated by testing a second or any number of additional genes or reporter gene constructs. Alternatively, expression of two or more genes or reporter gene constructs can be assayed simultaneously within the scope of this invention.

For the purposes of this invention, the term "quiescence" will be understood to encompass temporary cessation of cell growth and DNA replication such as occurs in cultured mammalian cells under conditions of serum starvation.

For the purposes of this invention, the term "senescence" will be understood to include permanent cessation of DNA replication and cell growth not reversible by growth factors, such as occurs at the end of the proliferative lifespan of normal cells or in normal or tumor cells in response to cytotoxic drugs, DNA damage or other cellular insult.

Senescence can be induced in a mammalian cell in a number of ways. The first is a natural consequence of normal cell growth, either in vivo or in vitro: there are a limited number of cell divisions, passages or generations that a normal cell can undergo before it becomes senescent. The precise number varies with cell type and species of origin (Hayflick & Moorhead, 1961, Exp. Cell Res. 25: 585–621). Another method for inducing senescence in any cell type is treatment with cytotoxic drugs such as most anticancer drugs, radiation, and cellular differentiating agents. See, Chang et al., 1999, Cancer Res. 59: 3761–3767. Senescence also can be rapidly induced in any mammalian cell by transducing into that cell a tumor suppressor gene (such as p53, p21, p16 or Rb) and expressing the gene therein. See, Sugrue et al., 1997, Proc. Natl. Acad. Sci. USA 94: 9648–9653; Uhrbom et al., 1997, Oncogene 15: 505–514; Xu et al., 1997, Oncogene 15: 2589–2596; Vogt et al., 1998, Cell Growth Differ. 9: 139–146

The reagents of the present invention include any mammalian cell, preferably a rodent or primate cell, more preferably a mouse cell and most preferably a human cell, that can induce expression of the p21 gene, wherein such gene is either the endogenous gene or an exogenous gene introduced by genetic engineering. Although the Examples disclose recombinant mammalian cells comprising recombinant expression constructs encoding such an inducible p21 gene, it will be understood that these embodiments are merely a matter of experimental design choice and convenience, and that the invention fully encompasses induction of endogenous p21.

In preferred embodiments, the invention provides mammalian cells containing a recombinant expression construct encoding an inducible mammalian p21 gene. In preferred embodiments, the p21 gene is human p21 having nucleotide and amino acid sequences as set forth in U.S. Pat. Nos. 5,424,400, incorporated by reference herein. In alternative embodiments, the p21 gene is an amino-terminal portion of the human p21 gene, preferably comprising amino acid residues 1 through 78 of the native human p21 protein (as disclosed in U.S. Pat. No. 5,807,692, incorporated by reference) and more preferably comprising the CDK binding domain comprising amino acids 21–71 of the native human p21 protein (Nakanishi et al., 1995, EMBO J. 14: 555–563). Preferred host cells include mammalian cells, preferably rodent or primate cells, and more preferably mouse or human cells. A particularly preferred embodiment are fibrosarcoma cells, more preferably human fibrosarcoma cells and most preferably human HT1080 fibrosarcoma cell line and derivatives thereof.

Recombinant expression constructs can be introduced into appropriate mammalian cells as understood by those with skill in the art. Preferred embodiments of said constructs are produced in transmissible vectors, more preferably viral vectors and most preferably retrovirus vectors, adenovirus vectors, adeno-associated virus vectors, and vaccinia virus vectors, as known in the art. See, generally, Mammalian Cell Biotechnology: a Practical Approach, (Butler, ed.), Oxford University Press: New York, 1991, pp. 57–84.

In additionally preferred embodiments, the recombinant cells of the invention contain a construct encoding an inducible p21 gene, wherein the gene is under the transcriptional control of an inducible promoter. In more preferred embodiments, the inducible promoter is responsive to a trans-acting factor whose effects can be modulated by an inducing agent. The inducing agent can be any factor that can be manipulated experimentally, including temperature and most preferably the presence or absence of an inducing agent. Preferably, the inducing agent is a chemical compound, most preferably a physiologically-neutral compound that is specific for the trans-acting factor. In the use of constructs comprising inducible promoters as disclosed herein, expression of p21 from the recombinant expression construct is mediated by contacting the recombinant cell with an inducing agent that induces transcription from the inducible promoter or by removing an agent that inhibits transcription from such promoter. A variety of inducible promoters and cognate trans-acting factors are known in the prior art, including heat shock promoters than can be activated by increasing the temperature of the cell culture, and more preferably promoter/factor pairs such as the tet promoter and fusions thereof with mammalian transcription factors (as are disclosed in U.S. Pat. Nos. 5,654,168, 5,851,796, and 5,968,773), and the bacterial lac promoter of the lactose operon and its cognate lacI repressor protein. In a preferred embodiment, the recombinant cell expresses the lacI repressor protein and a recombinant expression construct encoding human p21 under the control of a promoter comprising one or a multiplicity of lac-responsive elements, wherein expression of p21 can be induced by contacting the cells with the physiologically-neutral inducing agent, isopropylthio-β-galactoside. In this preferred embodiment, the lad repressor is encoded by a recombinant expression construct identified as 3'SS (commercially available from Stratagene, La Jolla, Calif.).

The invention also provides recombinant expression constructs wherein a reporter gene is under the transcriptional control of a promoter of a gene whose expression is modulated by p21. These include genes whose expression is induced by p21 and genes whose expression is repressed by p21. In preferred embodiments, the promoters are derived from genes whose expression is repressed by p21, and are identified in Table I. Most preferably, the promoter is derived from ORC1, PRC1, XRCC9, CDC2, cyclin B1, AIK1, CENP-A, CENP-F, MAD2, BUBR1, MCAK, HSET, CHL1, thymopoietin α, MNP2, MPP5, CDC47/MCM7, CDC21/MCM4, DNA ligase I, DNA polymerase α, Rad54, exonuclease HEX1/RAD2, or citron kinase. In additional preferred embodiments, the promoters are derived from genes whose expression is induced or otherwise increased by p21, and are identified in Table II. Most preferably, the promoter is derived from serum amyloid A, complement C3, connective tissue growth factor, integrin β-3, activin A, natural killer cell protein 4, prosaposin, Mac2 binding protein, galectin-3, superoxide dismutase 2, or cathepsin B. These reporter genes are then used as sensitive and convenient indicators of the effects of p21 induction, and enable compounds that inhibit or potentiate the effects of p21 expression in mammalian cells to be easily identified. Host cells for these constructs include any cell in which p21 gene expression can be induced, and preferably include cells also containing recombinant expression constructs containing an inducible p21 gene as described above. Reporter genes useful in the practice of this aspect of the invention include but are not limited to firefly luciferase, chloramphenicol acetyltransferase, beta-galactosidase, green fluorescent protein, and alkaline phosphatase.

In preferred embodiments, cells according to the invention comprise both a first recombinant expression construct encoding a reporter gone under the transcriptional control of a promoter for a mammalian gene whose expression is modulated by p21, and a second recombinant expression construct encoding a mammalian p21 gene, wherein p21 expression is experimentally-inducible thereby in the mammalian cell.

In alternative embodiments, the invention provides a mammalian cell comprising a recombinant expression construct encoding a reporter gene under the transcriptional control of a promoter for a mammalian gene whose expression is repressed by p21, wherein the promoter is from the gene ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, Rad54, exonuclease HEX1/RAD2, or citron kinase. In further alternative embodiments, the invention provides a mammalian cell comprising a recombinant expression construct encoding a reporter gene under the transcriptional control of a promoter for a mammalian gene whose expression is induced by p21, wherein the promoter is from the gene connective tissue growth factor, serum amyloid A, complement C3, integrin β-3, activin A, natural killer cell protein 4, prosaposin, Mac2 binding protein, galectin-3, superoxide dismutase 2, or cathepsin B.

The invention provides methods for identifying compounds that inhibit or promote senescence, whereby the effects of the compound are assayed by determining whether the compounds inhibit or potentiate induction or repression of genes whose expression is modulated by p21. In the practice of the methods of the invention, cultured mammalian cells in which p21 can be induced are treated to induce p21, for example, by radiation treatment or treatment with cytotoxic drugs, or transduced with a transmissible vector encoding p21. More preferably, p12-9 cells are used in which p21 can be induced by contacting the cells with IPTG. Typically, cells are grown in appropriate culture media (e.g., DMEM supplemented with 10% fetal calf serum (FCS) for p21-9 cells). p21 gene expression is induced in p21-9 cells by adding IPTG to the culture media at a concentration of about 50 μM. Typically, p21 is induced in these cells in the presence or absence of the compound to be tested according to the methods of the invention. mRNA is then isolated from cells in which p21 is induced, and expression of genes that are regulated by p21 is analyzed. Expression is compared in cells in which p21 is induced in the presence of the compound with expression induced in the absence of the compound, and the differences used to identify compounds that affect cellular gene expression according to the methods set forth herein. In certain embodiments, cellular gene expression is analyzed using microarrays of oligonucleotides or cellular cDNAs such as are commercially available (for example, from Genome Systems, Inc., St. Louis, Mo.). In alternative embodiments, genes known to be induced or repressed by p21 are assayed. Gene expression can be assayed either by analyzing cellular mRNA or protein for one or a plurality of p21-modulated genes. Most preferably, the genes used in these assays are genes identified in Tables I and II.

In alternative embodiments, such compounds are identified independently of p21-directed experimental manipulation. In such assays, cells are treated to induce senescence in any of the ways disclosed above, including but not limited to treatment with cytotoxic drugs, radiation or cellular differentiating agents, or introduction of a tumor suppressor gene. Expression of genes that are repressed or induced by p21 is analyzed in the presence or absence of the test compound. Most preferably, the genes used in these assays are genes identified in Tables I and II, using the types of mRNA and protein assays discussed above for gene expression analysis.

In alternative embodiments, the cells in which p21 is induced further comprise a recombinant expression construct encoding a reporter gene under the transcriptional control of a promoter of a cellular gene that is induced or repressed by p21. In preferred embodiments, the cellular gene is a gene that is repressed by p21, and the promoter is derived from a gene identified in Table I. Examples of known promoters for such genes include ORC1, PRC1, XRCC9, CDC2, cyclin B1, AIK1, CENP-A, CENP-F, MAD2, BUBR1, MCAK, HSET, CHL1, thymopoietin α, MPP2, MPP5, CDC47/MCM7, CDC21/MCM4, DNA ligase I, DNA polymerase α, RAD54, HEX1/RAD2, or citron kinase. In preferred embodiments, the cellular gene is a gene that is induced by p21, and the promoter is derived from a gene identified in Table II. Examples of known promoters for such genes include connective tissue growth factor, serum amyloid A, complement C3, integrin β-3, activin A, natural killer cell protein 4, prosaposin, Mac2 binding protein, galectin-3, superoxide dismutase 2, , or cathepsin B. Preferred reporter genes include but are not limited to firefly luciferase, β-galactosidase, alkaline phosphatase and green fluorescent protein, all of which are commercially available.

The invention also provides methods for identifying genes mediating the effects of p21-induced cellular senescence. Induction of p21 turns out to be an integral part of cell growth arrest associated with senescence, terminal differentiation and response to cellular damage. As described in the Examples below, cDNA array hybridization was used to investigate whether these effects were due to p21-induced changes in gene expression. This analysis showed that p21 selectively inhibited multiple genes involved in the control of mitosis, DNA replication, segregation and repair. Many proteins that were induced by p21 in these experiments have been associated with senescence and aging or implicated in age-related diseases, including atherosclerosis, Alzheimer's disease, amyloidosis and arthritis. These findings suggest that cumulative effects of p21 induction may contribute to the pathogenesis of cancer and age-related diseases. In addition, a number of p21-activated genes encode secreted proteins with potential paracrine effects on cell growth and apoptosis. In agreement with this observation, conditioned media from p2l-induced cells showed mitogenic and anti-apoptotic activity.

The analyses disclosed in the Examples below showed that inhibition of cell cycle progression genes was not simply a consequence of p21-induced growth arrest. Shutoff of some of these genes occurred together with cell growth arrest, and the re-expression of all the tested genes upon release from p21 preceded the re-entry of cells into cell cycle. The nature of the immediate-response genes, such as ORC1 (required for the initiation of DNA replication), topoisomerase II (which is central to DNA segregation in G2), and PLK1 (involved in the initiation of mitosis), suggested that inhibition of their expression may in fact play a causal role in the induction of growth arrest by p21. These observations formed the basis for one aspect of the methods of the invention, which provide methods for identifying genes involved in cell cycle progression in mammalian cells.

Furthermore, the biological functions of both immediate- and early-response genes indicate that their shutoff serves to maintain p21-induced growth arrest. The use of the reagents and methods of the present invention has demonstrated that release from p21-induced growth arrest results in endoreduplication and mitotic abnormalities. DNA replication and mitosis did not resume after release from IPTG until all the p21-inhibited genes were re-expressed, and DNA replication resumed considerably before mitosis. The results disclosed in the Examples below indicate that prolonged p21 induction leads to the decay of many proteins involved in cell cycle progression, including a number of proteins involved in the "quality control" of replication or mitosis. As a result of failing to regenerate the pools of such proteins by the time cells re-entered the cell cycle after release from p21, abnormal replication and abnormal mitosis ensued. For example, the production of polypolid cells was observed after release from prolonged p21-induced cell growth arrest. Endoreduplication, the process that leads to polyploidization of the cells, may be a consequence of the abrogation of mitotic checkpoint control (Hixon et al., 1998, *Mol. Cell Biol.* 18: 6224–37), which could result from a lack of p21-inhibited checkpoint control proteins, such as MAD2 and BUBR1. Furthermore, polyploid cells may arise due to a failure of cytokinesis that can be triggered by a lack of cytokinesis-associated proteins Prc1, Aim1 and citron kinase, which we found to be inhibited by p21.

Figure 7:
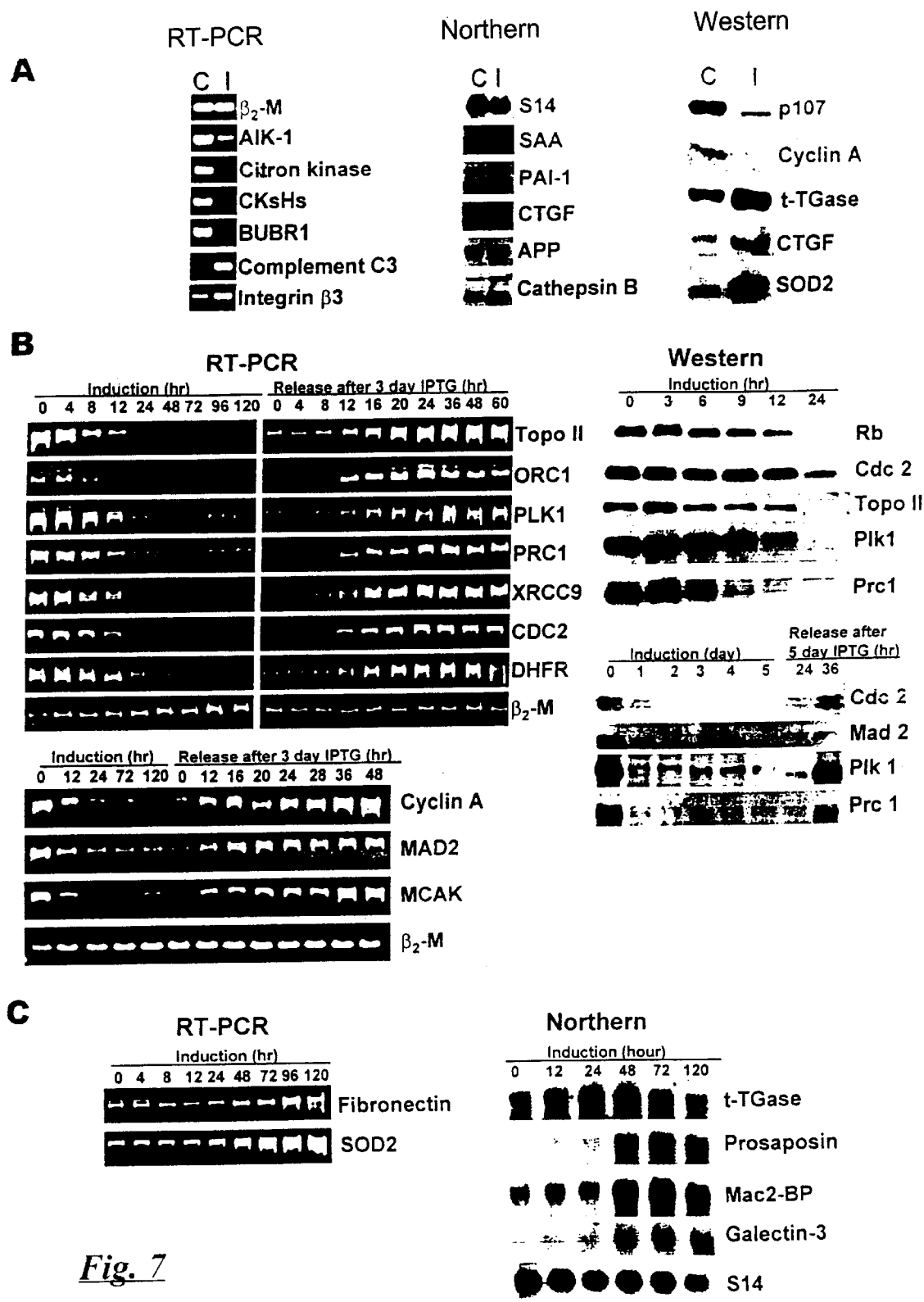
FIG. 7A are photographs of gel electrophoresis patterns of RT-PCR experiments (left), northern blot analysis of cellular mRNA expression (middle) and immunoblotting assays for IPTG-induced changes in expression of the denoted genes; C: control untreated p21-9 cells; I: cells treated for 3 days with 50 μM IPTG. β2-microglobuln (β2-M) was used as a normalization control for RT-PCR and S14 ribosomal protein gene for northern hybridization.
FIG. 7B are photographs of gel electrophoresis of RT-PCR experiments (left) and immunoblotting analysis (right) showing the time course of changes in the expression of the denoted p21-inhibited genes upon IPTG addition and release.
FIG. 7C are photographs of gel electrophoresis patterns of RT-PCR experiments (left) and northern hybridization analysis (right) of the time course of changes in the expression of the denoted p21-induced genes upon IPTG addition.
FIG. 7D is a comparison of gene expression in untreated control p21-9 cells (C), serum-starved quiescent cells (Q) and IPTG-treated senescent cells (I).
Figure 7D:
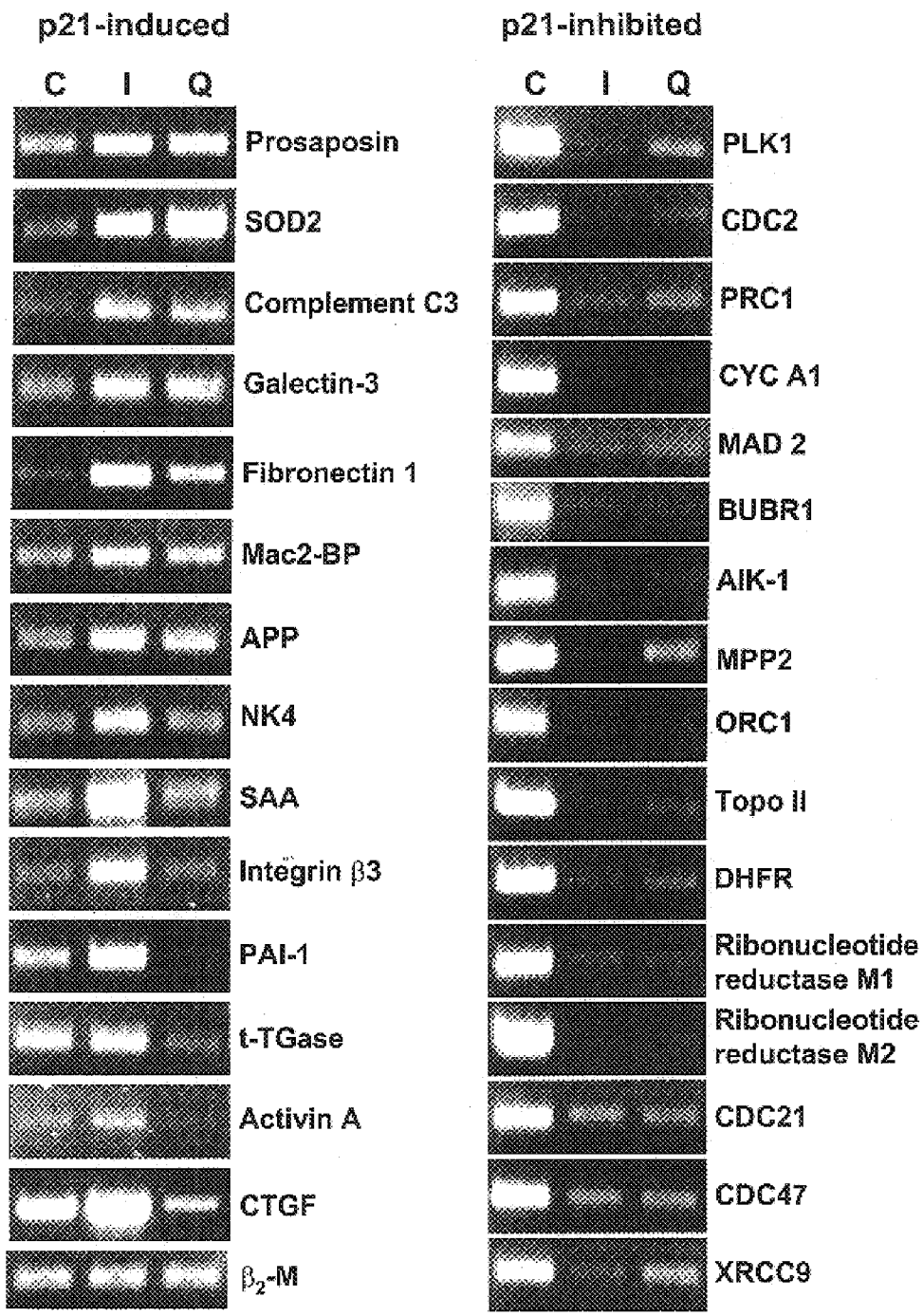

Different mitotic abnormalities that were observed after release from p21 have been previously found to result from mutation or inhibition of proteins that control proper chromosome alignment and segregation, including the products of such p21-inhibited genes as MAD2, BUBR1, PLK1, AIK-1, CENP-A, CHL1 and MCAK (Li & Benezra, 1996, *Proc. Natl. Acad. Sci. USA* 93: 10436–10440; Glover et al., 1998, *Genes Develop.* 12: 3777–3787; Chan et al., 1999, *J. Cell Biol.* 146: 941–954 ). The role of such proteins in p21-induced mitotic abnormalities is supported by the analysis of the time course of decay and resynthesis of mitosis control proteins. Thus, at the time of resumed mitosis (36 hrs after release), the pools of Cdc2 and Plk1, which are required for the initiation of mitosis, are regenerated to levels comparable to untreated cells (as shown in FIG. 7B). In contrast, MAD2, the function of which is to prevent anaphase unless chromosomes are properly attached to the mitotic spindle, is resynthesized much less efficiently (FIG. 7B). Furthermore, MAD2 levels that remain after one day of IPTG treatment are much higher than after 3 or more days (FIG. 7B), which agrees with a lower frequency of abnormal mitosis in cells that are released after one day of p21 induction.

p21 overexpression has been reported to inhibit DNA repair (Pan et al., 1995, *J. Biol. Chem.* 270: 22008–22016; Umar et al., 1996, *Cell* 87: 65–73). In light of our results, this effect of p21 can be attributed to the inhibition of DNA repair genes, such as XRCC9, RAD54, HEX1/RAD2, RAD21 homolog and DNA ligase I. Inhibition of DNA repair is also likely to increase the frequency of mutations in cells that recover from p21-induced growth arrest, contributing to the overall genetic instability of such cells.

p21-induced genetic destabilization in normal cells may also have a potential carcinogenic effect. Growth arrest of senescent cells is triggered by transient p21 induction, while another CDK inhibitor, p16, appears to be responsible for maintaining the growth arrest after the decay of p21 (Alcorta et al., 1996, *Proc. Natl. Acad. Sci. USA* 93: 13742–13747). p16 (in striking contrast to p21) is frequently mutated in human tumors (Hall & Peters, 1996, *Adv. Cancer Res.* 68: 67–108), including HT1080 fibrosarcoma used in the present study. If the primary carcinogenic effect of p16 mutations is abortive senescence, then cells expressing mutated p16 would experience prolonged p21 induction. Consistent with the results disclosed herein, re-entry into the cell cycle under these conditions would be expected to result in the development of karyotypic abnormalities. Unlike p16, p21 would act more as an oncogene than as a tumor suppressor in this process, which can explain the rarity of p21 mutations in cancer.

Thus, the invention provides methods for identifying compounds having an anticarcinogenic effect by inhibiting p21-induced cell cycle arrest. The compounds produced by these methods would be expected to be able to minimize the development of cells having karyotypic abnormalities, which in turn would be expected to reduce the likelihood that such cells would develop into malignant disease.

The invention also provides methods for identifying compounds that induce or promote senescence. In this aspect, the invention provides compounds that increase inhibition of genes inhibited by p21 expression. Inhibition of cell division and cell cycle progression control genes is shown herein to prevent cells from re-entering the cell cycle after p21 induction and result in irreversible growth arrest. Thus, compounds that induce or potentiate p21-induced repression of such genes are effective in promoting cell senescence and terminal growth arrest. Thus, the invention provides methods for identifying compounds that inhibit cellular genes that control cell cycle progression, most preferably genes identified in Table I. In preferred embodiments, the compounds are used to promote senescence of mammalian cells, most preferably tumor cells, hyperplastic cells or any cell type that is pathological or disease-causing due to excessive proliferation. In preferred embodiments of this aspect of the invention, the methods comprise the steps of inducing p21 in a mammalian cell in the presence or absence of the compound; assaying the cell for expression of genes repressed by p21; and identifying the compound as a potentiator of senescence if the genes are repressed to a greater extent in the presence of the compound than in the absence of the compound. In other aspects of the methods of the invention, compounds that promote senescence in a mammalian cell are identified independently of p21-directed experimental manipulation, for example, by inducing senescence in the cells in any of the ways disclosed above. It is known in the art that senescence can be induced even in p21-deficient cells (Chang et al., 1999, Oncogene 18: 4808–4818 and Pantoja et al., 1999, Oncogene 18: 4974–4982) and that some senescence-inducing treatments, such as the treatment of MCF-7 cells with all-trans retinoic acid (Chang et al., 1999, Cancer Res. 59: 3761–3767), are associated with a decrease rather than an increase in the cellular levels of p21 (Zhu et al., 1997, Exp. Cell Res. 234: 293–299).

The invention also provides methods for potentiating senescence in a mammalian cell, comprising the step of contacting the cell with a compound identified by the methods of the invention. In preferred embodiments, the mammalian cells are tumor cells, hyperplastic cells or any cell type that is pathological or disease-causing due to excessive proliferation. In alternative embodiments, the methods comprise the additional step of contacting the cells with radiation or anticancer, cytotoxic or antiproliferative drugs.

The observed effects of p21 induction on gene expression show numerous correlations with the changes that have been associated with cell senescence and organism aging. Some of these correlations come from the analysis of p21-inhibited genes. Thus, senescent fibroblasts were reported to express lower levels of Rb (Stein et al., 1999, Mol. Cell. Biol. 19: 2109–2117), as we have also observed upon p21 induction. It is also interesting that three p21-inhibited genes, CHL1, CDC21 and RAD54 encode members of the helicase family. A deficiency in another protein of the helicase group has been identified as the cause of Werner syndrome, a clinical condition associated with premature aging and, at the cellular level, accelerated senescence of cells in culture (Gray et al., 1997, Nature Genet. 17: 100–103).

The strongest correlations with the senescent phenotype, however, come from identification of p21-induced genes, many of which are known to increase their levels during replicative senescence or organism aging. Overexpression of ECM proteins is a known hallmark of replicative senescence, and two p21-induced genes in this group, fibronectin 1 and plasminogen activator inhibitor 1 (PAI-1), have been frequently associated with cellular senescence (reviewed in Crisofalo & Pignolo, 1996, Exp. Gerontol. 31: 111–123). Other p21-induced genes that were also reported to be overexpressed in senescent fibroblasts include tissue-type plasminogen activator (t-PA)(West et al., 1996, Exp. Gerontol. 31: 175–193), cathepsin B (diPaolo et al., 1992, Exp. Cell Res. 201: 500–505), integrin β3 (Hashimoto et al., 1997, Biochem. Biophys. Res. Commun. 240: 88–92) and APP (Adler et al., 1991, Proc. Natl. Acad. Sci. USA 88: 16–20). Expression of several p21-induced proteins was shown to correlate with organism aging, including t-PA and PAI-1 (Hashimoto et al., 1987, Thromb. Res. 46: 625–633), cathepsin B (Bernstein et al., 1990, Brain Res. Bull. 24: 43–549) activin A (Loria et al., 1998, Eur. J. Endocrinol. 139: 487–492), prosaposin (Mathur et al., 1994, Biochem. Mol. Biol. Int. 34: 1063–1071), APP (Ogomori et al., 1988, J. Gerontol. 43: B157–B162), SAA (Rosenthal & Franklin, 1975, J. Clin. Invest. 55: 746–753) and t-TGase (Singhal et al., 1997, J. Investig. Med. 45: 567–575).

The most commonly used marker of cell senescence is the SA-β-gal activity (Dimri et al. ,1995, Proc. Natl. Acad. Sci. USA 92: 9363–9367). This gene is strongly elevated in IPTG-treated p21-9 cells (Chang et al., 1999, Oncogene 18: 4808–4818). SA-β-gal was suggested to represent increased activity and altered localization of the lysosomal β-galactosidase (Dimri et al., 1995, ibid.), and other studies have described elevated lysosome activities in senescent cells (Cristofalo & Kabakijan, 1975, Mech. Aging Dev. 4: 19–28). Five lysosomal enzymes appear in Table 2, including N-acetylgalactosamine-6- sulfate sulfatase (GALNS), cathepsin B, acid α-glucosidase, acid lipase A and lysomal pepstatin-insensitive protease. p21 also upregulated genes for mitochondrial proteins SOD2, metazin and 2, 4-dienoyl-CoA reductase, which correlates with reports of different mitochondrial genes overexpresssed in senescent cells (Doggett et al., 1992, Mech. Aging Dev. 65: 239–255; Kodama et al., 1995, Exp. Cell Res. 219: 82–86; Kumazaki et al., 1998, Mech. Aging Dev. 101: 91–99).

As disclosed in the following Examples, there are many similarities between the effects of p21 induction in p21-9 cells and changes associated with senescence in normal fibroblasts. Senescent cells, in particular, were shown to overproduce different growth factors and ECM proteins that may promote metastasis (Campisi et al., 1998, J. Investig. Dermatol. Symp. Proc. 3: 1–5). Several growth factors and growth factor receptors have also been identified among the genes that are induced by irradiation in a p53-dependent manner, under the conditions of strong p21 induction (Komarova et al., 1998, Oncogene 17: 1089–1096). Interestingly, most of these genes did not contain p53-binding sites in their promoters. Our results suggest that induction of growth factors by p53 may be an indirect effect, mediated through p21 induction.

Thus, the invention provides methods for identifying genes associated with cellular senescence, particularly genes that are induced during senescence, and particularly by p21 expression. The invention also provides methods for identifying compounds that can inhibit p21-mediated induction of such genes. Such compounds would be expected to exhibit the capacity to reduce, repress or reverse cellular senescence by their effects on p21-mediated induction of gene expressions.

Strikingly, products of many genes that we found to be induced by p21 have been linked to age-related diseases, including Alzheimer's disease, amyloidosis, atherosclerosis and arthritis. Thus, APP gives rise to β-amyloid peptide, the main component of Alzheimer's amyloid plaques. Complement C3 (Veerhuis et al., 1995, Virchows Arch. 426: 603–610) and AMP deaminase (Sims et al., 1998, Neurobiol. Aging 19: 385–391) were also suggested to play a role in Alzheimer's. It is especially interesting that t-TGase, which is most rapidly induced by p21 and which has been described as a pleiotropic mediator of cell differentiation, carcinogenesis, apoptosis and aging (Park et al., 1999, *J. Gerontol. A Biol. Sci.* 54: B78-B83), is involved in the formation of plaques associated with both Alzheimer's disease and amyloidosis (Dudek & Johnson, 1994, Brain Res. 651: 129–133). The latter disease is due to the deposition of another p21-induced gene product, SAA, which has also been implicated in atherosclerosis, osteoarthritis and rheumatoid arthritis (Jensen & Whitehead, 1998, *Biochem. J.* 334: 489–503). Two other p21-upregulated secreted proteins, connective tissue growth factor (CTGF) and galectin 3 are involved in atherosclerosis (Oemar et al., 1997, *Circulation* 95: 831–839; Nachtigal et al., 1998, *Am. J. Pathol.* 152: 1199–1208). In addition, cathepsin B (Howie et al., 1985, *J. Pathol.* 145: 307–314), PAI-1 (Cerinic et al., 1998, *Life Sci.* 63: 441–453), fibronectin (Chevalier, 1993, *Semin. Arthritis Rheum.* 22: 307–318), GALNS and Mac-2 binding protein (Seki et al., 1998, *Arthritis Rheum.* 41: 1356–1364) have been associated with osteoarthritis and/or rheumatoid arthritis. Furthermore, senescence-related changes in ECM proteins, such as increased PAI-I expression, were proposed to result in age-specific deterioration in the structure of skin and other tissues (Campisi, 1998, *J. Investig. Dermatol. Symp. Proc.* 3: 1–5). Increased fibronectin production by aging cells was also suggested to increase the density of the fibronectin network in ECM, which may contribute to slower would healing in aged individuals (Albini et al., 1988, *Coll. Relat. Res.* 8: 23–37).

The results disclosed herein indicate that p21 induction affects cellular gene expression in a way that may increase the probability of the development of cancer or age-related diseases. A surge of p21 expression occurs not only in normal replicative senescence but also in response to cellular damage; in both cases, the undesirable effects of p21 induction would be expected to accumulate in an age-dependent manner. Elucidation of specific molecular interactions and regulatory pathways that are responsible for these effects of p21 on gene expression may suggest new approaches to the prevention of cancer and age-related diseases.

Thus, the invention provides methods for identifying genes associated with age-related diseases. The invention also provides methods for identifying compounds that can inhibit p21-mediated induction of such genes. Such compounds would be expected to exhibit therapeutic capacity to prevent, retard or reverse age-related diseases.

The methods of the invention directed towards identifying genes whose expression is modulated by p21 take advantage of the ability to experimentally induce p21 expression. Cells as provided by the invention containing inducible p21 genes can be used to isolate cellular mRNA reflecting the expression status of genes induced, repressed and unchanged by p21 expression. Naive cells in which p21 is not induced provide a comparative, control source of cellular mRNA. A plurality of nucleic acids, most preferably cDNA copies of cellular mRNA, can be obtained that is specific for either induced or repressed genes by constructing differential cDNA libraries using subtractive hybridization methods. See, for example, Diatchenko et al., 1996, *Proc. Natl. Acad. Sci. USA* 93: 6025–6030. mRNA or cDNA isolated before and after p21 induction can also be used as probes for hybridization analysis, either using arrayed or non-arrayed cDNA libraries, and differentially-expressed genes can be identified from such hybridization. See, generally, Sambrook et al., 1990, *Molecular Cloning: a Laboratory Manual*, Cold Spring Harbor Laboratory Press: New York. Alternatively, differential display of the subtracted cDNA population can be performed to yield sets of genes that are either upregulated or downregulated by p21 expression.

In additional embodiments, genes that are upregulated or downregulated by p21 expression can be isolated using molecular cloning techniques well known in the art. Sambrook et al., ibid. Differential cDNA libraries produced as described above can be screened with probes specific for genes induced or repressed by p21, using subtractive hybridization methods that enrich the probes for the appropriate cDNA population. Alternatively, such probes can be used to screen conventionally-prepared cDNA libraries constructed to maximize the percentage of colonies comprising full-length or close to full length cDNAs, to facilitate cloning of p21-modulated genes, particularly novel genes identified using the methods of the invention. Said genes are also intended to fall within the scope of this invention.

The following Examples are intended to further illustrate certain preferred embodiments of the invention and are not limiting in nature.

EXAMPLE 1

Production of a Mammalian Cell Comprising an Inducible p21 Gene

A recombinant derivative of human fibrosarcoma cell line HT1080, p21-9, was produced essentially according to Chang et al. (1999, *Oncogene* 18: 4808–4818, incorporated by reference herein). This cell line contained a p21 coding sequence under the transcriptional control of a promoter regulated by isopropyl-β-thiogalactoside (IPTG). Expression of p21 can be induced by culturing these cells in the presence of a sufficient amount of IPTG, thereby permitting the sequellae of p21 expression to be studied in the absence of any additional effects that induction of the endogenous p21 gene might provoke. This cell line has been deposited in the American Type Culture Collection (A.T.C.C.), Manassas, Va. and given Accession Number Briefly, a subline of HT1080 expressing a murine ecotropic retrovirus receptor and a modified bacterial lacI repressor encoded by the plasmid 3'SS (Stratagene) (described in Chang & Roninson, 1996, *Gene* 33: 703–709, incorporated by reference) was infected with retroviral particles containing recombinant retrovirus LNp21CO3, the structure of which is shown in FIG. 1. This retroviral vector contains the bacterial neomycin resistance gene (neo) under the transcriptional control of the retroviral long terminal repeat promoter. p21-encoding sequences are cloned in the opposite orientation to the transcriptional direction of the neo gene, and under the control of a modified human cytomegalovirus promoter. Specifically, the CMV promoter contains a three-fold repeat of bacterial lac operator sequences that make expression from the promoter sensitive to the lacI repressor expressed in the cell. LNp21CO3 was constructed by cloning a 492 bp fragment of DNA comprising the p21 coding sequence into the NotI and BglII sites of the parent vector, LNXCO3 (disclosed in Chang & Roninson, ibid.).

After infection, cells infected with the LNp21CO3X vector were selected by culturing the cells in the presence of 400 μg/mL G418 (obtained from BRL-GIBCO, Gaithersburg, Md.). Clonal line p21-9 was derived from LNp2ICO3 transduced, G418-resistant cell lines by end-point dilution until a clonal cell line was obtained.

EXAMPLE 2

Figure 2:
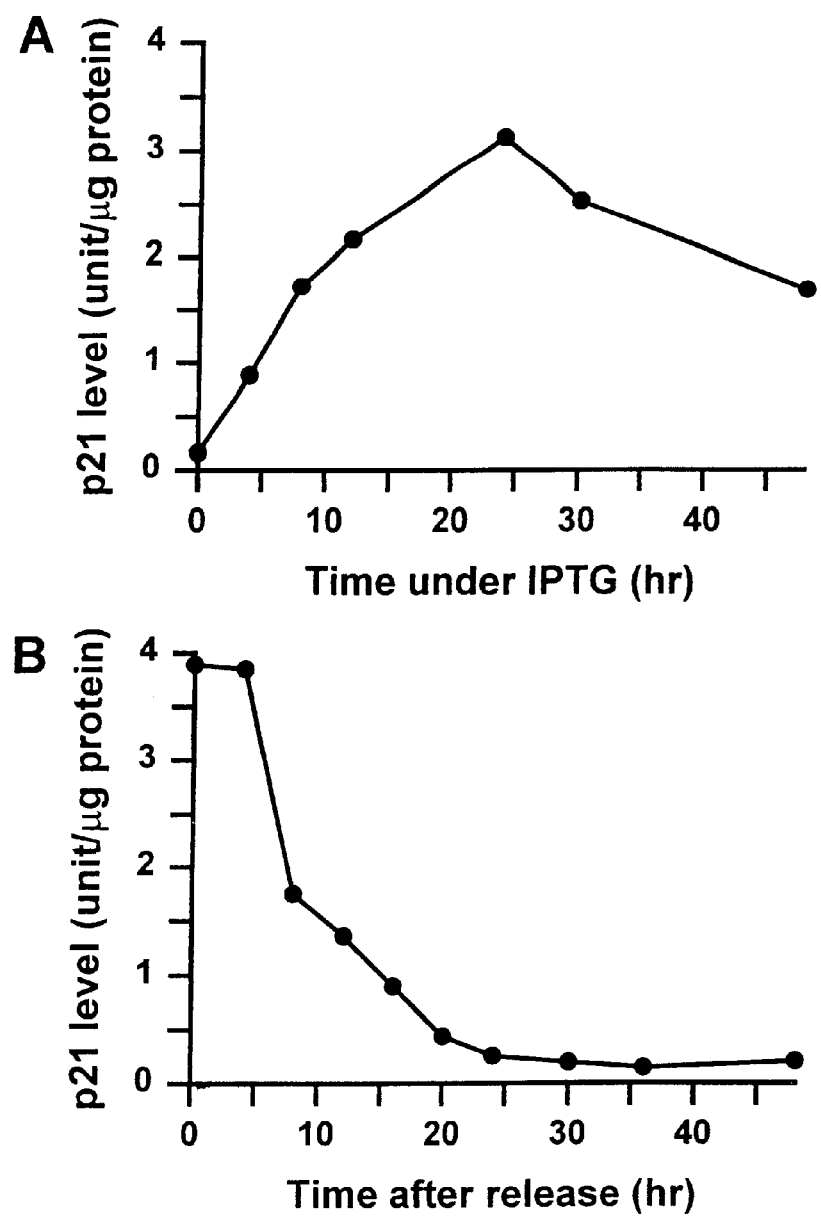
FIG. 2A is a graph of the time course of p21 induction after the addition of 50 μM IPTG, where p21 levels were determined by ELISA.
FIG. 2B is a graph of the time course of p21 decay after removal of IPTG.

Cell Growth Assays p21-9 cells produced as described in Example 1 were used in cell growth assays to determine what changes in cell growth occurred when p21 was expressed in the cell.

p21 expression from the LNp21CO3 vector in p21-9 cells was induced by culturing the cells in DMEM medium containing 10% fetal calf serum (Hyclone, Logan, Utah) and IPTG. Results of these assays are shown in FIGS. 2A and 2B. FIG. 2A shows the time course of p21 protein production in cells cultured in the presence of 50 μM IPTG. p21 gene expression increased between 6 and 12 hours after introduction of IPTG into the growth media, which expression peaked at about 24 hours post-induction. Upon removing the cells from IPTG-containing media, p21 expression fell about as rapidly as it had risen, returning to pre-induction levels at about 24 hours after IPTG was removed, (FIG. 2B).

Figure 3:
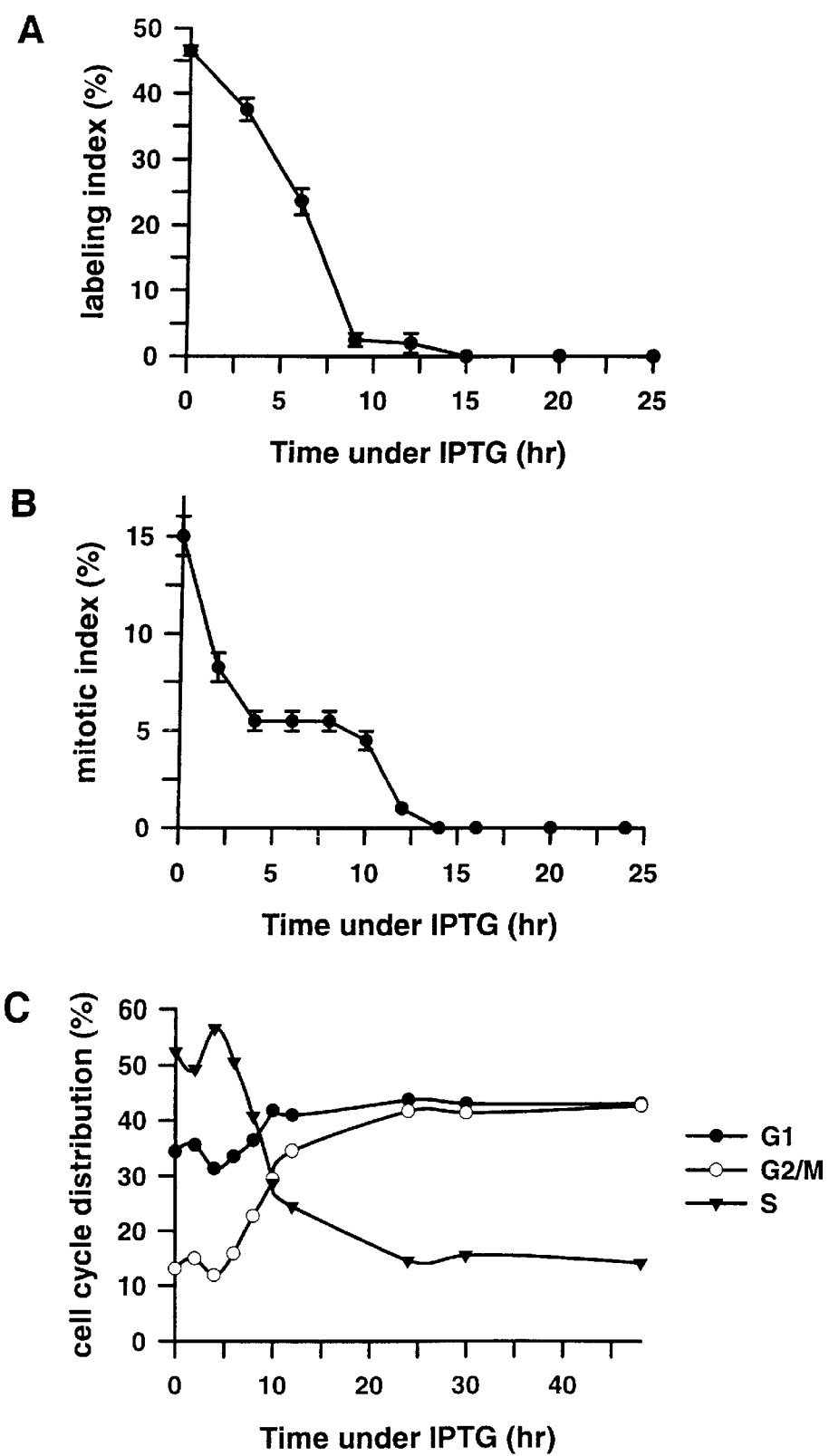
FIG. 3A is a graph of the time course of changes in $^3$H-thymidine labeling index (as determined by autoradiography) after the addition of 50 μM IPTG.
FIG. 3B is a graph of the time course of changes in mitotic index (as determined by microscopy after DAPI staining) after the addition of 50 μM IPTG.
FIG. 3C is a graph of the time course of changes in cell cycle distribution (determined by fluorescence-activated cell sorting (FACS) analysis following propidium iodide) after the addition of 50 μM IPTG; -●-: cells in G1 phase of the cell cycle; -○-: cells in G2/M phase of the cell cycle; -▼-: cells in S phase of the cell cycle.

Cell growth in the presence of IPTG was assayed in three ways: measuring $^3$H-thymidine incorporation (termed the "labeling index"); observing the number of mitotic cells in the culture by microscopy (termed the "mitotic index") and determining the distribution of the culture cells in different portions of the cell cycle (termed the "cell cycle distribution"). These results are shown in FIGS. 3A through 3C.

$^3$H-thymidine incorporation assays were performed substantially as described by Dimri et al. (1995, *Proc. Natl. Acad. Sci. USA* 92: 9363–9367). Cells were cultured in the presence of $^3$H-thymidine for 3h, and then analyzed by autoradiography. DNA replication as determined by autoradiography ceased entirely by 9 hours after addition of IPTG to the culture media (FIG. 3A).

The mitogenic index was determined by observing cells microscopically and calculating the number of cells in mitosis after staining with 5 μg/mL 4,6-diamino-2-phenylindole (DAPI), and images were collected using a Leica DMIRB fluorescence microscope and Vaytek (Fairfield, Iowa) imaging system. Microscopically-detectable mitotic cells disappeared from these cultures in the presence of IPTG in two stages: the first occurring between 0–4 hours after IPTG addition (wherein the mitotic index dropped from about 15% in untreated cells to about 5% in IPTG-treated cells) and then again between about 10–14 hours after IPTG addition (wherein the mitotic index dropped to zero at about 13 hours after IPTG addition (FIG. 3B).

Cell cycle distribution was determined using FACS analysis of DNA content after staining with propidium iodide as described by Jordan et al. (1996, *Cancer Res.* 56: 816–825) using Becton Dickinson FACSort. Cell cycle distribution stabilized after 24 hrs of IPTG treatment (shown in FIG. 3C). By this time, 42–43% of IPTG-treated cells were arrested in G1 and G2, respectively, and about 15% of the cells were arrested with S-phase DNA content.

The effects of p21 expression were also investigated by releasing cells from the effects of p21 by removing IPTG from the cell culture media. It was known that IPTG-treated p21-9 cells displayed morphological senescence markers (Chang et al., 1999, ibid.). As shown in FIG. 2B, p21 gene expression levels in p21-9 cells reverted to basal levels within 24 hours after removal of IPTG. Here, it was determined whether IPTG-treated p21-9 cells show any loss of clonogenic capacity after removal of IPTG. The results of these experiments are shown in FIGS. 4A through 4D.

Figure 4:
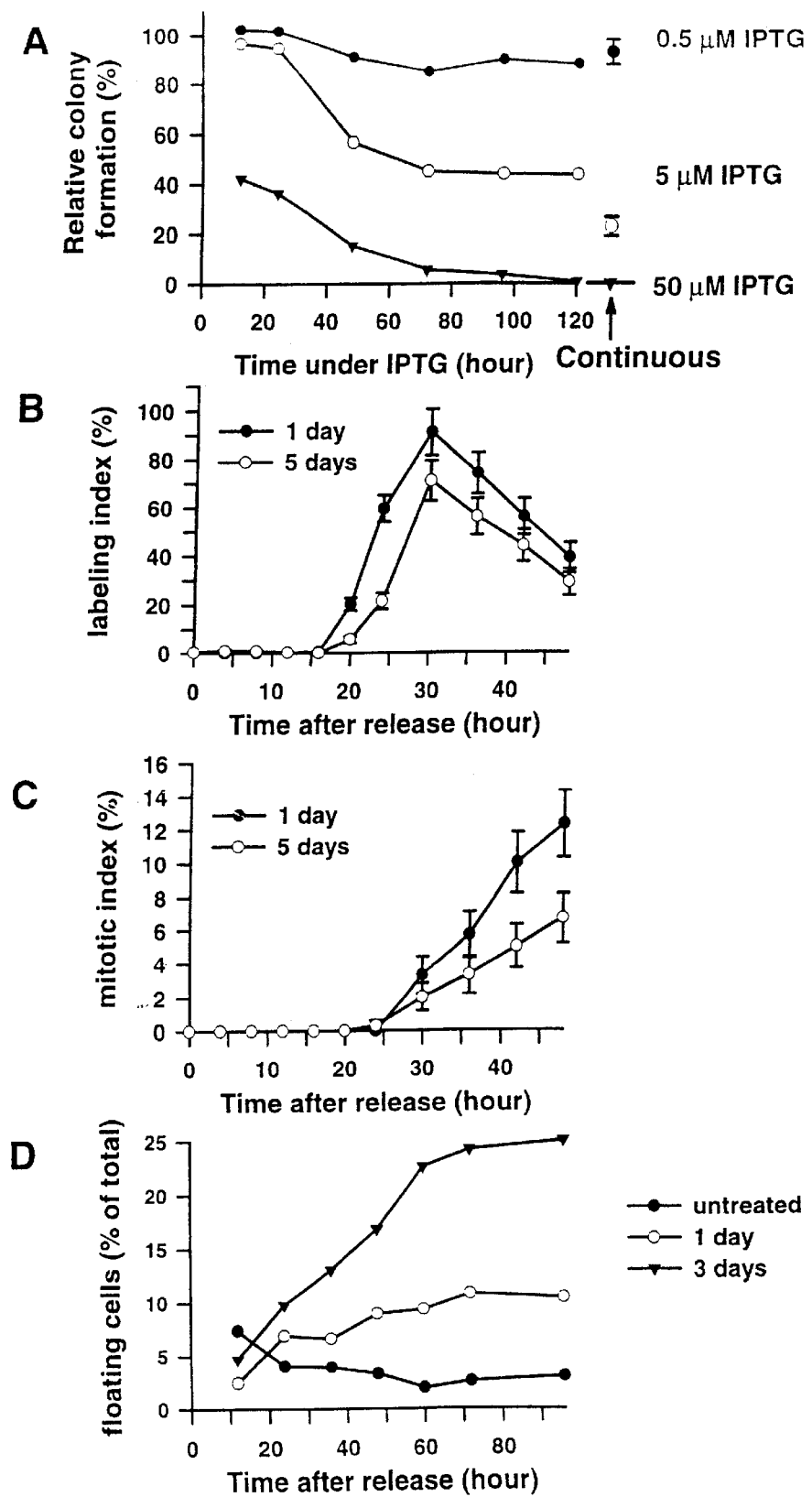
FIG. 4A is a graph showing the effects of the duration of treatment with different doses of IPTG on colony formation by p21-9 cells; -●-: 0.5 μM IPTG; -○-: 5 μM IPTG; -▼-: 50 μM IPTG.
FIG. 4B is a graph of the time course of changes in $^3$H-thymidine labeling index (determined by autoradiography) after the removal of 50 μM IPTG; -●-: 1 day; -○-: 5 days.
FIG. 4C is a graph of the time course of changes in mitotic index (determined by microscopy) after the removal of 50 μM IPTG; -●-: 1 day; -○-: 5 days.
FIG. 4D is a graph of the time courses of changes in the percentage of floating cells after the removal of 50 μM IPTG following one day or three days of treatment; -●-: untreated; -○-: 1 day; -▼-: 3 days.

Colony assays for recovery from IPTG treatment were performed by plating about 2,000 p21-9 cells per 10 cm culture dish in DMEM/10% FCS and the presence or absence of IPTG. Cells were allowed to form colonies for 10 days before their clonogenic capacity was determined. p12-9 cells were treated with three concentrations of IPTG: 0.5 μM, 5 μM and 50 μM. These treatments induced, respectively, no measurable increase over basal p21 levels (0.5 μM), half-maximal (5 μM) or maximal increase (50μM) in p21 gene expression. As shown in FIG. 4A, treatment of p21-9 cells with 0.5 μM IPTG did not inhibit colony formation. In contrast, continuous exposure of the cells to 5 μM or 50 μM IPTG reduced the clonogenicity of p2l-9 cells by 80% and 100%, respectively. When IPTG was removed after 12 or 14 hours, cells treated with 5 μM IPTG showed substantially undiminished colony formation. However, the 50 μM IPTG-treated cells showed a decrease in clonogenicity of 58–63%. After 3–5 days treatment, cells cultured in 5 μM IPTG showed a decreased clonogenicity of 55–58%, and cells cultured in 50 μM IPTG showed a decreased clonogenicity of 95–99%. These results indicated that the ability of cells to recover after p21 gene expression decayed was inversely correlated with the level of induced p21 and with the duration of p21 induction. This result was consistent with results obtained by others in other cell culture systems (Fang et al., 1999, *Oncogene* 18: 2789–2797).

The causes of the loss of clonogenicity were investigated as follows. Resumption of DNA replication was first detected about 20 hours after release from IPTG using the $^3$H-thymidine incorporation assay as described above. These results are shown in FIG. 4B. Resumption of mitosis in these cells was first detected about 30 hours after IPTG release, as determined from the mitotic index as described above. These results are shown in FIG. 4C. The percentages of cells entering the S or M phase of the cell cycle were higher in cells that were treated with IPTG for one day than for five days (compare the curves for each in FIGS. 4B and 4C) but the differences were not significant enough to account for the corresponding difference in clonogenic recovery as shown in FIG. 4A.

Figure 5:
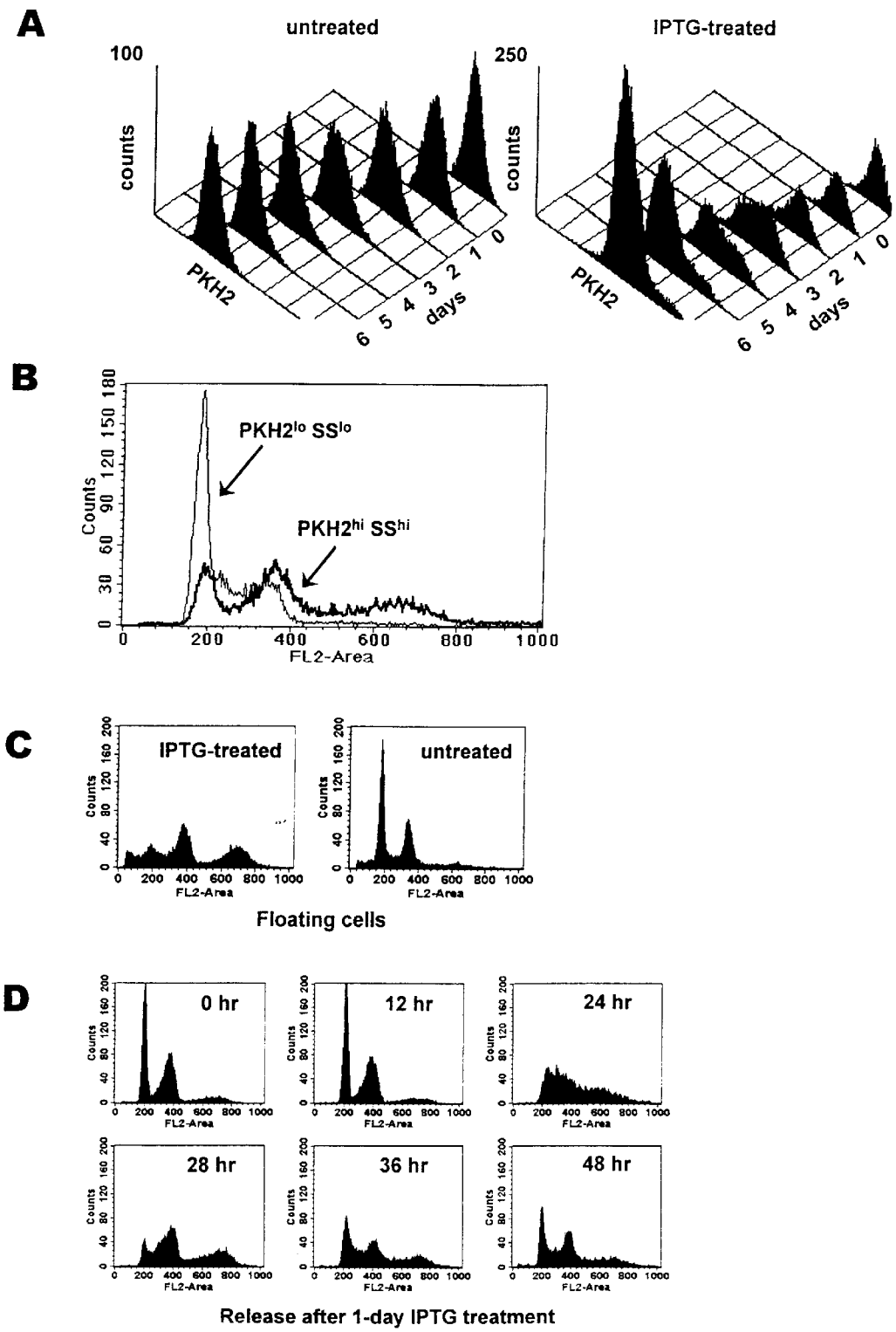
FIG. 5A is a histogram showing changes in PKH2 fluorescence profiles of untreated cells (left) and cells treated for 5 days with 50 μM IPTG and released in IPTG-free media (right), as determined by FACS.
FIG. 5B is a graphical representation of FACS profiles of DNA content of PKH2$^{lo}$SS$^{lo}$ (thin line) and PKH2$^{hi}$SS$^{hi}$ (thick line) cell populations isolated by FACS after 5-day treatment with 50 μM IPTG, PKH2 labeling, and 6-day growth without IPTG.
FIG. 5C is a graphical representation of FACS profiles of DNA content of floating cells, collected 48 hrs after release from 3-day treatment with 50 μM IPTG (left) and from untreated cells (right).
FIG. 5D is a graphical representation of FACS profiles of DNA content of attached cells at 0h, 12h, 24h, 28h, 36h and 48h after release from 1-day IPTG treatment.

Microscopic examination of culture plates from the clonogenic assays showed that plates treated with 50 μM IPTG for three or more days contained numerous single cells and small cell clusters that failed to develop into colonies. In addition, release from IPTG was associated with the appearance of floating cells during the first two days after IPTG release, and the number of such cells was much higher when cells were released after three days of IPTG induction than after one day (as shown in FIG. 4D). Most of these floating cells were dead, as indicated by trypan blue staining and a 100–1,000-fold decrease in clonogenicity The effect of p21 induction in these cells was further studied by examining the DNA content of growth-retarded and dead cells that appeared after release from prolonged IPTG treatment. Growth-retarded cells were isolated using FACS on the basis of increased retention of PKH2, a lipophilic fluorophore that stably incorporates into the cell membrane and is evenly divided between daughter cells; this leads to a proportional decrease in cellular fluorescence with each round of cell division, and no decrease in non-dividing or dead cells (Horan & Slezak, 1989, *Nature* 340: 167–168). These assays were performed as described in Chang et al. (1999, *Cancer Res.* 59: 3761–3767). Untreated p21-9 cells and cells treated with 50 μm IPTG for five days were labeled with PKH2, plated in IPTG-free medium, and their PKH2 fluorescence was analyzed on consecutive days. As shown in FIG. 5A, IPTG-treated cells started dividing later than the control cells and developed a heterogeneous PKH2 profile, with an emerging peak of proliferating cells and a shoulder of growth-retarded cells with high PKH2 fluorescence. The growth-retarded cells also showed elevated side scatter which is characteristic for senescent cells (Chang et al., 1999, ibid.). The proliferating (PKH2$^{lo}$SS$^{lo}$) and growth-retarded (PKH2$^{hi}$SS$^{hi}$) cell populations were separated by FACS six days after release from IPTG, and their DNA content was analyzed by P1 staining. The growth-retarded fraction differed from the proliferating cells in having a higher G2/M fraction and a large number of cells with greater than 4C DNA content (shown in FIG. 5B). The polyploid nature of the latter cells was confirmed by fluorescence in situ hybridization (FISH) of interphase nuclei with specific probes for chromosomes 18 and 21; these experiments were performed as described in Chang et al. (1999, ibid.). High polyploid and G2/M fractions were also observed among floating dead cells collected after release from IPTG (shown in FIG. 5C); microscopic analysis indicated that many of these dead cells were in mitosis.

To investigate the origin of polyploid cells, the time course of changes in DNA content of the entire cell population after release from IPTG was determined. The number of polyploid cells greatly increased 24–28 hrs after release (as shown in FIG. 5D), concurrently with the resumption of DNA synthesis (compare, FIG. 4B). This result indicated that many of the released cells were undergoing endoreduplication, an unscheduled round of DNA replication. The time course and magnitude of endoreduplication were very similar, however, between cells released after one day (FIG. 5D) or after 3–5 days of IPTG inhibition.

Figure 6:
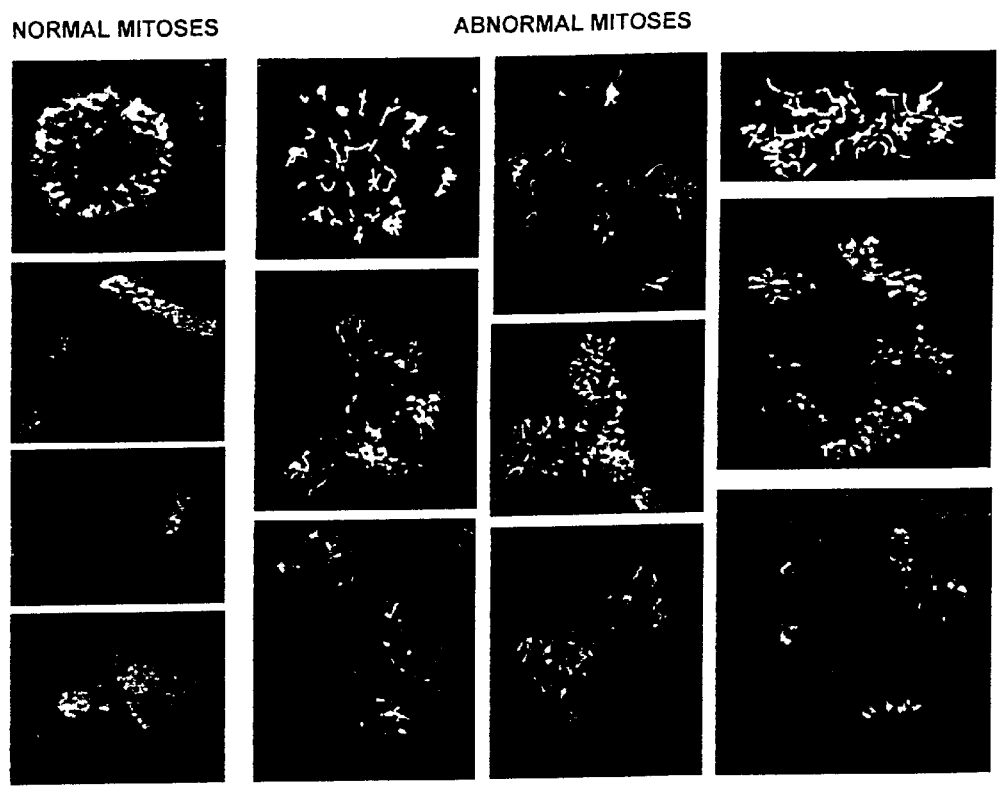
FIG. 6 are photomicrographs illustrating examples of normal (left) and abnormal (right) mitotic figures observed 1–2 days after release from IPTG (DAPI staining; photographed at 1,000×magnification.

A major difference between cells that were inhibited by IPTG for one day compared with those inhibited for S days emerged, however, when the morphology of attached mitotic cells arising 1–2 days after release from IPTG was examined. These results are shown in FIG. 6. While an overwhelming majority of mitotic figures in untreated cells appeared morphologically normal (FIG. 6, left), most of the mitotic figures in cells released after IPTG treatment showed numerous abnormalities, including multicentric mitosis, uneven chromosome distribution and prophase arrest (FIG. 6, right). The percentage of normal mitoses in 1-day and 5-day IPTG treated cells were 45% and 2%, respectively, which is close to the corresponding values for clonogenic recovery (38% and 1%). These results suggest that abnormal mitosis, together with endoreduplication, are responsible for the loss of clonogenicity after release from p21.

These results indicated that induced expression of p21 has profound effects not only on the cells while the gene is expressed, but effects that linger and interfere with normal recovery of the cells into the cell cycle and growth.

EXAMPLE 3

Analysis of Gene Expression Modulated by p21 Gene Expression

The results disclosed in Example 3 suggested that the morphological and cell cycle consequences of p21 induction could be the result of repression of genes that control cell cycle progression. The effects of p21 induction on cellular gene expression were examined as follows.

Reverse transcription-polymerase chain reaction (RT-PCR) analysis was performed to investigate expression of genes known to be involved in the control of cell cycle checkpoint progression. Preliminary RT-PCR analysis of 27 genes involved in cell cycle control and DNA replication revealed that eight of these genes were inhibited by IPTG in p21-9 cells. Total RNA was extracted from p21-9 cells collected at different time points during IPTG treatment and release. RT-PCR analysis of changes in gene expression for downregulated genes was carried out essentially as described by Noonan et al. (1990, Proc. Natl. Acad. Sci. USA 87: 7160–7164).

A more comprehensive analysis was performed by isolating poly(A)$^-$ RNA from untreated p21-9 cells and from cells that were treated for 3 days with 50 μm IPTG. cDNA was prepared from the poly(A)$^+$ RNA and used as probes for differential hybridization with the Human UniGEM V cDNA microarray. (as performed by Genome Systems, Inc., St. Louis, Mo.), which contains over 4,000 sequence-verified known human genes and 3,000 ESTs. More than 2,500 genes and ESTs showed measurable hybridization signals with probes from both untreated and IPTG-treated p21-9 cells. Genes that were downregulated with balanced differential expression $\geq 2.5$ or upregulated with balanced differential expression $\geq 2.0$ are listed in Tables 1 and 2, respectively.

Expression of 69 of these genes was individually tested by RT-PCR or northern hybridization with probes derived from inserts of the cDNA clones present in the microarray; these cDNAs were obtained from Genome Systems, Inc. In addition, enzyme-linked immunosorbent assay (ELISA) measurement of p21 protein was carried out using WAF1 ELISA kit (obtained from Oncogene Science, Uniondale, N.Y.) as described (Chang et al., 1999, Oncogene 18: 4808–4818). The following primary antibodies were used for immunoblotting: mouse monoclonal antibodies against Cdc2 (Santa Cruz), cyclin A (NeoMarkers), Plk 1 (Zymed) and Rb (PharMingen); rabbit polyclonal antibodies against MAD2 (BadCo), p107 (Santa Cruz), CTGF (Fisp-12; a gift of Dr. L. Lau), Prc 1 (a gift of Drs. W. Jiang and T. Hunter), and topoisomerase IIα (Ab0284; a gift of Dr. W. T. Beck), and sheep polyclonal antibody against. SOD2 (Calbiochem). Horse radish peroxidase (HRP)-conjugated secondary antibodies used were goat anti-mouse and goat anti-rabbit. IgG (Santa:Cruz) and rabbit anti-sheep IgG (KPL). Protein concentrations in all samples were equalized after measurement with BioRad-protein assay kit. Immunoblotting was carried out by standard procedures, and the signal was detected by chemiluminescence using LumiGlo (KPL).

These results are shown in FIGS. 7A through 7C. The changes in gene expression predicted by the microarray assays described above were confirmed for 38/39 downregulated and 27/30 upregulated genes. The observed signal differences in northern hybridization or RT-PCR for most of the tested genes (FIG. 7A through 7C) appeared to be higher than the values of balanced differential expression determined from the cDNA array (Tables 1 and 2), suggesting that cDNA array hybridization tends to underestimate the magnitude of p21 effects on gene expression. Changes in the expression of 6 downregulated and 4 upregulated genes were also tested at the protein level by immunoblotting (FIG. 7B) or zymography (not shown) and were confirmed in all cases tested.

It was recognized that p21-mediated changes in gene expression were comprised of near-term effects and longer-tern effects that followed p21-induced cell growth arrest. For this purpose, the time course of changes in the RNA levels of a subset of p21-inhibited (FIG. 7B) and p21-induced genes (FIG. 7C) after the addition and removal of IPTG was determined. Immunoblotting was used to analyze the time course of p21-induced changes in Rb phosphorylation (as indicated by electrophoretic mobility) and in the cellular levels of Rb and several proteins that were inhibited by p21 according to the cDNA array; these results are shown in FIG. 7B. Rb was found to become dephosphoryfated as early as 6 hrs after the addition of IPTG. Furthermore, Rb.protein levels decreased sharply between 12–24 hrs (shown in FIG. 7B), but no significant changes were detected in RB mRNA levels (data not shown). A similar decrease was observed for a Rb-related protein p107 (shown in FIG. 7A).

A. Gene Expression Inhibited by p21.

All the tested p21-inhibited genes showed a rapid response to p21 induction and release. Five of these genes (topoisomerase IIα, ORC1, PLK1, PRC1 and XRCC9) showed significant inhibition at both RNA and protein levels between 4 and 8 hrs after the addition of IPTG (FIG. 7B). This pattern has been termed an "immediate response," which parallels the kinetics of cell growth arrest and Rb dephosphorylation. Other p21-inhibited genes (such as CDC2 or DHFR) showed an "early response" pattern that lags slightly behind the cessation of DNA replication and mitosis, with a major decrease in mRNA levels detectable only 12 hrs after the addition of IPTG. All p21-inhibited genes, however, resumed their expression 12–16 hrs after the removal of IPTG, when the cells were still growth-arrested and before the resumption of DNA replication and mitosis (FIG. 7B). This analysis indicated that changes in the expression of p21-inhibited genes were near-term effects of p21 induction and release and were not a consequence of cell growth arrest and recovery.

In summary, 69 genes and 3 ESTs were identified by the cDNA microarray as downregulated in p21-induced cells, with balanced differential expression of 2.5–12.6 (Table 1A); 5 additional genes identified by our earlier assays as downregulated in IPTG-treated cells are listed in Table 1B. A strikingly high fraction of downregulated genes identified by, the cDNA array (43 of 69) were associated with mitosis, DNA replication, segregation and repair and chromatin assembly, indicating a highly selective nature of p21-mediated inhibition of gene expression.

The largest group of p21-downregulated genes are that have been implicated in the signaling, execution and control of mitosis. These genes include CDC2 and cyclin B1 that form the mitosis-initiating complex, polo-like kinase (PLK1) that plays a role in the onset of mitosis, mitotic checkpoint control and cytokinesis (Glover et al., 1998, *Genes Develop.* 12: 3777–3787) and CDC2-interacting protein CKsHs1, a target of mitotic checkpoint control (Hixon et al., 1998, *Mol. Cell Biol.* 18: 6224–37). Other genes in this group encode a homolog of Xenopus condensin protein XCAP-H, a homolog of Rad21 repair protein involved in sister chromatid cohesion (Losada et al., 1998, *Genes Develop.* 12: 1986–1997) and mitotic recombination (McKay et al., 1996, *Genomics* 36: 305–315), a centrosome-associated kinase AIK1 involved in spindle formation (Kimura et al., 1997, *J. Biol. Chem.* 272: 13766–13771), centromere proteins CENP-A and CENP-F, as well as MAD2 and BUBR1 proteins that play a central role in the spindle checkpoint control (Li and Benezra, 1996, *Science* 274: 246–248; Chan. et al., 1999, *J. Cell Biol.* 146: 941–954), mitotic centromere-associated kinesin (MCAK), kinesin-like protein HSET located at the interphase centrosome and mitotic spindle, CHL1 helicase (a homolog of a yeast protein that plays a role in proper chromosore distribution during-mitosis; Gerring et al., 1990, *EMBO J.* 9: 4347–4358), and three proteins involved in cytokinesis, Prc1, Aim1/Aik2 and citron kinase (Jiang et al., 1998, *Mol. Cell* 2: 877–885; Terada et al., 1998, *EMBO J.* 17: 667–676; Madaule et al., 1988, *Nature* 394: 491–494). p21 also inhibits genes that encode nuclear envelope proteins lamin B1 and lamin B2, lamin-associated polypeptides α (thymopoietin α) involved in nuclear assembly, and M-phase phosphoproteins MPP2 aMPP5. Deficiencies in many of the above proteins are known to result in abnormal chromosome segregation and polyploidization, the same events that we observed in p12-9 cells after release from IPTG.

Many p21-inhibited genes are involved in DNA replication and segregation, chromatin assembly and DNA repair. Some of these genes encode enzymes involved in nucleotide biosynthesis, including ribonucleotide reductase subunits M1 and M2, thymidine kinase, thymidylate synthase, uridine phosphorylase and dihydrofolate reductase. Other proteins are involved in DNA. replication, including components of the replication licensing factor Cdc47/Mcm4, Cdc45 homolog, Orc1 protein of the origin recognition complex, DNA polymerase a, B-Myb, 37-kD subunit of replication factor C, and DNA ligase I. This group also includes genes involved in the segregation of replicated DNA (topoisomerase IIα), inheritance of epigenetically determined chromosomal states (p60 subunit of chromatin assembly factor-I), and other chromatin components, such as high mobility group proteins 1 and 2. Several p21-inhibited genes are associated with DNA repair, including XRCC9, which may be involved in DNA post-replication repair or cell cycle checkpoint control (deWinter et al, 1998, *Nat Genet.* 20: 281–283), Rad54 recombination repair protein, exonuclease Hex1/Rad2, and the above Rad21 homolog and DNA ligase 1.

Over 60% of p21-inhibited genes in the cDNA array are involved in mitosis; DNA replication, segregation and repair. Such biological selectivity is unprecedented in large-scale expression profiling studies. A corollary to this observation is that p21-inhibited genes whose function is presently unknown are likely to play a role in cell cycle progression. Indeed, six p21-inhibited genes were originally listed in the cDNA array as ESTs or genes with unknown function, but a database search has linked three of their products to cell division of DNA repair. In one case, the originally identified EST was found to map in a genomic clone 3' to the coding sequence of citron kinase; inhibition of the citron kinase gene by p21 was then demonstrated by RT-PCR based on its coding sequence. Cloning of additional p21-inhibited genes is likely to yield novel genes that play a role in mammalian cell division.

These results also suggest further opportunities for discovering components of the cellular program of p21-induced senescence that would be targets for therapeutic intervention. It has been suggested that p21-mediated inhibition of gene expression is a result of E2F inhibition (de Toledo et al., 1998, *Cell Growth Differ.* 2: 887–896). In agreement with this interpretation, a subset of our p21-inhibited genes (e.g. CDC2, ORC1, DHFR, cyclin A1) contain E2F sites in their promoters. On the other hand, no E2F sites could be found in the promoters of some p21-inhibited genes (e.g. cyclin B1), and some E2F-dependent genes (e.g. cyclin E) were unaffected by p21 induction (data not shown). Some as yet unidentified regulatory factors, in addition to E2F, may therefore be involved in p21-mediated inhibition of gene expression. Such additional factors represent targets for novel pharmaceuticals, the existence and identity of said targets being available for elucidation using the methods and reagents provided by the instant invention.

B. Gene Expression Induced by p21

In addition to genes repressed by p21 expression, the assays described above detected genes induced by p21. The pattern of gene expression of p2l-induced genes is shown in FIG. 7C. In contrast to p21-inhibited genes, p21-upregulated genes increased their expression only 48 hrs after the addition of IPTG, i.e. after the onset of growth arrest in all cells. Only one tested gene, tissue transglutaminase (t-TGase), showed a detectable increase 12 hrs after the addition of IPTG, but its expression reached a maximum only by 48 hrs (as shown in FIG. 7C). Furthermore, elevated expression of all the tested genes (except for t-TGase) persisted for at least three days after release from IPTG, well after resumption of the cell cycle (not shown). This "late response" kinetics indicated that p21 induction of such genes was a delayed effect relative to p21-mediated growth arrest.

48 known genes and 6 ESTs or genes with-unknown functions were identified as upregulated in p21-induced cells, with balanced differential expression of 2.0–7.8 (Table 2). A very high fraction (20/48) of identifiable genes in this group encode extracellular matrix (ECM) components (e.g. fibronectin 1, laminin b2, Mac-2 binding protein), other secreted proteins (e.g. activin A, connective tissue growth factor, serum amyloid A), or ECM receptors (such as integrin b3). Several of these secreted proteins, as well as a large group of p21-induced intracellular proteins (Table 2), are known to be induced in different forms of stress response or to play a role in stress-associated signal transduction. Remarkably, many genes that we found to be induced by p21 are also upregulated in cellular senescence, organism aging, or different age-related diseases.

In contrast to p21-inhibited genes, none of the genes found to be induced by p21 have any known functions that may trigger cell growth arrest. Furthermore, the induction of such genes is a late response that lags far behind the onset of growth arrest. Interestingly, several p21-induced genes are positively regulated by NFκB, including superoxide dismutase 2 (SOD2) (Jones et al., 1997, *Mol. Cell. Biol.* 17: 6970–6981), t-TGase (Mirza et al., 1997, *Amer. J. Physiol.* 272: G281–G288), Alzheimer's β-amyloid precursor protein (APP) (Grilli et al., 1996, *J. Biol. Chem.* 271: 15002–15007) and the inflammatory protein serum amyloid A (SAA) (Jensen and Whitehead, 1998, *Biochem J.* 334: 489–503). Since p21 activates NFκB-dependent transcription through its effect on the transcription cofactor p300 (Perkins et al., 1997, *Science* 275: 523–527), it is possible that activation of p300 or related transcription cofactors may be responsible for the effect of p21 on some of the upregulated genes. The delayed kinetics of p21-mediated induction of gene expression suggest, however, that this induction occurs far downstream of the immediate effects of p21.

These results, and the nature of the genes set forth in Table 2, indicate that expression of these genes is not involved in the growth arrest function of p2 . However, the abundance of secreted proteins that we found among the products of p21-activated genes has important physiological consequences. As disclosed in Example 5 below, conditioned media from p21-induced cells exhibits two biological effects predicted by the nature of p21-upregulated genes: stimulation of cell growth and suppression of apoptosis. This finding, taken with the above discussed genetic destabilization in p21-induced cells, suggests that "paracrine" effects of p21 may contribute to carcinogenesis through a tumor-promoting effect on neighboring cells. This raises the possibility that suppression of p21-mediated gene induction may provide a way to achieve an anti-carcinogenic effect, and that p21-mediated gene induction pathways are targets of rational drug design for a new generation of cancer-preventing drugs.

The observed paracrine, anti-apoptotic effect of p21 induction agrees with the reported activities of prosaposin and galectin-3, secreted proteins that we found to be induced by p21 (Table 2). Anti-apoptotic activity has also been associated-with p21-induced intracellular proteins SOD2 (Manna et al.,.1998, *J. Biol. Chem.* 273: 13245–13254) and R-Ras (Suzuki et al., 1998, *FEBS Lett.* 437: 112–116). Paradoxically, p21-induced t-TGase and cathepsin B (Singhal et al., 1997, *J. Investig. Med.* 45: 567–575) have been ascribed a pro-apoptotic function. There are conflicting reports in the literature regarding the effects of p21 on apoptosis. In some systems, p21 overexpression induced apoptosis (Prabhu et al., 1996, *Clin. Cancer Res.* 2: 1221–1229; Tsao et al., 1999, *J. Virol.* 73: 4983–4990), but in other studies p21 protected cells from apoptosis induced by several types of treatment (Gorospe et al., 1997, *Oncogene* 14: 929–935; Lu et al., 1998, *Oncogene* 16: 705–712;Bissonnette & Hunting, 1998, *Oncogene* 16: 3461–3469). The results disclosed herein that p21 induces both anti-apoptotic and pro-apoptotic genes may explain the contradictory reports on the effects of p21 on apoptosis.

EXAMPLE 4

Identifying the Specificity of p21 Induction by Comparing IPTG-treated and Serum-Starved p21-9 Cells The identity of p21-induced changes in cellular gene expression that are likely to be a consequence of cell growth arrest was determined as follows. Analogous experiments were performed using a truncated form of p21 (comprising amino acids 1–90) and identical results were obtained.

Growth arrest (quiescence) was induced in p21-9 cells by serum starvation produced by culturing the cells in serum-free media for 4 days. In serum-starved cells, unlike IPTG-treated p21-9 cells, the cells did not develop a senescent morphology and showed only very weak SA-β-gal expression. p21 levels in serum-starved cells were increased only about 2-fold, as opposed to the 15–20 fold increase seen in IPTG-treated cells. FIG. 9 shows RT-PCR analysis performed as described above of the expression of a group of p21-inhibited and p21-induced genes in p21-9 cells that were growth- arrested after 4 days in serum-free media or 3 days in the presence of 50 $\mu$M IPTG. Genes that were completely inhibited in p21-9 cells when the culture media contained 50 $\mu$M IPTG were also inhibited in serum-starved cells, but most of these genes were inhibited to a lesser extent than in IPTG-treated cells.

Genes whose expression is induced by p21 showed three distinct patterns. The first group are genes whose expression is induced as strongly in quiescent cells as in senescent cells. These include galectin-3, superoxide dismutase 2, complement C3 and prosaposin, indicating that their induction was a consequence of cell growth arrest or that such genes were exquisitely sensitive to slightly elevated p21 levels. The second group are genes that were up-regulated in quiescent cells but not as strongly as in senescent cells. These genes include fibronectin-1, Mac2 binding protein and the Alzheimer precursor protein serum amyloid A. The third group are genes that are not detectably induced in quiescent cells but are strongly induced in senescent cells. These genes include CTGF, plasminogen activator inhibitor 1, tissue transglutaminase or natural killer cell marker protein NK4, integrin beta 3 and activin A.

The difference between the response of certain genes to induction of quiescence by serum starvation and cellular senescence through IPTG-induced overexpression of p21 identified these genes as diagnostic markers of senescence. Furthermore, novel senescence markers can now be identified by comparing their expression between p21-expressing and quiescent cells.

EXAMPLE 5

Production of Conditioned Media Containing Mitogenic Factors and Mitogenic Activity Assays Several p21-upregulated secreted proteins act as growth factors, including CTGF (Bradham et al., 1991, *J. Cell Biol.*

114: 1285–1294), activin A (Sakurai et al., 1994, *J. Biol. Chem.* 269: 14118–14122), epithelin/granulin (Shoyab et al., 1990, *Proc. Natl. Acad. Sci. USA* 87: 7912–7916) and galectin-3 (Inohara et al., 1998, *Exp Cell Res.* 245: 294–302), suggesting that p21 induction may cause paracrine mitogenic effects. In addition, galectin-3 (Akahani et al., 1997, *Cancer Res.* 57: 5272–5276) and prosaposin (Hiraiwa et al., 1997, *Proc. Natl. Acad. Sci. USA* 94: 4778–4781) were shown to have anti-apoptotic activity. Conditioned media from IPTG-treated p21-9 cells was tested to investigate whether it would have an effect on cell growth and apoptosis.

In these experiments, conditioned media were prepared by plating $10^6$ p12-9 cells per 15 cm plate in the presence of DMEM/10% FCS. The next day, IPTG was added to a final concentration of 50 $\mu$M, and this media was replaced three days later with DMEM supplemented with 0.5% FCS and 50 $\mu$M IPTG. Two days later (days 3–5 of IPTG treatment), this conditioned media was collected and stored at 4° C. up to 15 days before use. Control media were prepared by adding IPTG-free DMEM/0.5% FCS to untreated cells grown to the same density as IPTG-treated cells and collecting the media two days thereafter.

The slow-growing human fibrosarcoma cell line HS 15.T was used to detect mitogenic activity in these conditioned media. For mitogenic activity assays, both types of conditioned media, as well as fresh media and 1:1 mixtures of conditioned media and fresh media were used to test mitogenic activity. In these experiments, the conditioned media were supplemented with 1% or 2% FCS. Briefly, HS 15.T cells were plated in 12-well plates at 15,000 cells per well. Two days later, these cells were cultured in different types of media. The cells were grown in conditioned media for 60 hr, and the $^3$H-thymidine at a concentration of 3.13 $\mu$Ci/mL was added and incubated for 24 hrs. Cells were then collected and their $^3$H-thymidine incorporation determined as described by Mosca et al. (1992, *Mol. Cell. Biol.* 12: 4375–4383).

Figure 8:
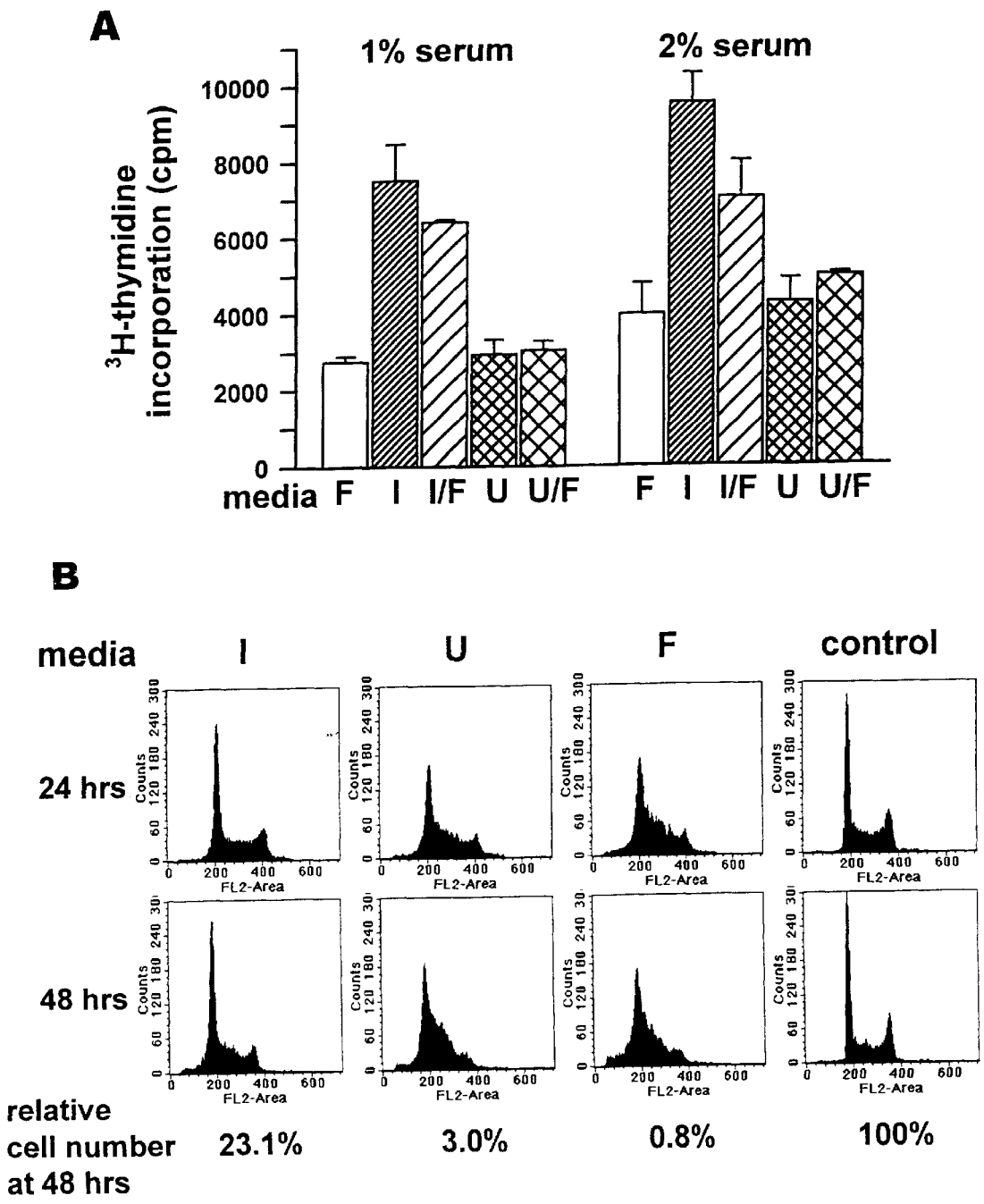
FIG. 8A is a histogram showing the effects of fresh media (F), conditioned media from IPTG-treated (I) or untreated p21-9 cells (U), and 1:1 mixtures of conditioned and fresh media (I/F and U/F), supplemented with 1% or 2% serum, on $^3$H-thymidine incorporation by HS 15.T cells.
FIG. 8B are graphical representations of FACS profiles of the DNA content of combined attached and floating C8 cells after 24 hr or 48 hr incubation in 10% serum (control), in low-serum fresh media (F) or in conditioned media from IPTG-treated (I) or untreated (U) p12-9 cells. Relative numbers of attached cells (as determined by methylene blue staining) after 48 hr incubation in the same media are listed beneath each set of histograms.

The addition of IPTG to fresh media had no effect in this assay (not shown). As shown in FIG. 8A, there was no significant difference between cell growth in fresh media and in conditioned media from untreated p21-9 cells. In contrast, conditioned media from IPTG-treated cells increased $^3$H-thymidine incorporation up to three-fold (FIG. 8A). Growth stimulation of HS 15.T by conditioned media from IPTG-treated cells was also detectable by methylene blue staining (data not shown).

The effect of this conditioned media on apoptosis was also determined. These experiments used a mouse embryo fibroblast line C8, immortalized by E1A. This cell line is highly susceptible to apoptosis induced by different stimuli (Lowe et al., 1994, *Science* 266:. 807–810; Nikiforov et al. 1996, *Oncogene* 13: 1709–1719), including serum starvation (Lowe et al., 1994, *Proc. Natl. Acad. Sci. USA* 91: 2026–2030). Apoptosis was analyzed by plating 3×10$^5$ C8 cells per 6-cm plate, and replacing the media on the following day with fresh media supplemented with 0.4% serum or with conditioned media (no fresh serum added). DNA content analysis and DAPI staining were carried out after 24 hrs and 48 hrs, and relative cell numbers were measured by methylene blue staining (Perry et al., 1992, *Mutai. Res.* 276: 189–197) after 48 hrs in low-serum media.

The addition of low-serum fresh media or conditioned media from IPTG-treated or untreated cells rapidly induced apoptosis in C8 cells, as evidenced by cell detachment and apoptotic morphology detectable in the majority of cells after DAPI staining (not shown). Conditioned media from IPTG-treated cells, however, strongly increased cell survival relative to fresh media and conditioned media from untreated cells, as measured by methylene blue staining of cells that remained attached after 48 hrs (as shown in FIG. 8B). The effect of the conditioned media from p21-induced cells was even more apparent in FACS analysis of cellular DNA content, which was carried out on combined attached and floating C8 cells 24 hrs and 48 hrs after media change (FIG. 8B). Unlike many other cell lines, apoptosis of C8 cells produces only a few cells with decreased (sub-G1) amount of DNA, and it is characterized by selective disappearance of cells with G2/M DNA content (Nikiforov et al., 1996, ibid.). Serum-starved cells in conditioned media from IPTG-treated cells retained the G2/M fraction and showed cell cycle profiles that resembled control cells growing in serum-rich media (FIG. 8B). The addition of IPTG by itself had no effect on apoptosis in C8 cells (not shown). Thus, p21 induction in HT1080 cells results in the secretion of mitogenic and anti-apoptotic factors, as predicted by the nature of p21-unregulated genes.

It should be understood that the foregoing disclosure emphasizes certain specific embodiments of the invention and that all modifications or alternatives equivalent thereto are within the spirit and scope of the invention as set forth in the appended claims.

TABLE 1

Genes downregulated by p21 induction

A. p21-inhibited genes identified by UniGemV array:

| Genes | Accession No. | Balanced Diff. Expr. | Confirmed by[a] |
|---|---|---|---|
| Associated with mitosis: | | | |
| CDC2 | X05360 | 2.5 | R, W |
| CKsHs1 (CDC2 kinase) | X54941 | 5.5 | R |
| PLK1 (polo-like kinase) | U01038 | 5.1 | R, W |
| XCAP-H condensin homolog | D38553 | 6 | R |
| CENP-A (centromere protein A) | U14518 | 5.3 | R |
| CENP-F (centromere protein F) | U30872 | 2.5 | R |
| MAD2 | U65410 | 6.6 | R, W |
| BUBR1 | AF053306 | 5.9 | R |
| MCAK (mitotic centromere-associated kinesin) | U63743 | 3.8 | R |

TABLE 1-continued

| Genes downregulated by p21 induction | | | |
|---|---|---|---|
| HSET kinesin-like protein | AL021366 | 3.6 | R |
| CHL1 helicase | U75968 | 3.3 | R |
| AIK-1 (aurora/IPL1-related kinase) | D84212 | 4.6 | R |
| AIM-1 (AIK-2; aurora/IPL1-related kinase) | AF004022 | 10.2 | R |
| PRC1 (protein regulating cytokinesis 1) | AF044588 | 12.6 | R, W |
| Citron kinase | H10809 | 2.7 | R |
| Lamin B1 | L37747 | 7 | |
| Lamin B2 | M94362 | 2.7 | |
| LAP-2 (lamin-associated protein 2) | U18271 | 4.6 | R |
| MPP2 (M phase phosphoprotein 2) | U74612 | 3.7 | R |
| MPP5 (M phase phosphoprotein 5) | X98261 | 3.7 | |
| Associated with DNA replication, segregation and chromatin assembly: | | | |
| Thymidine kinase 1 | K02581 | 2.9 | R |
| Thymidylate synthase | X02308 | 3.9 | R |
| Uridine phosphorylase | X90858 | 2.5 | |
| Ribonucleotide reductase M1 | X59543 | 4.6 | R |
| Ribonucleotide reductase M2 | X59618 | 10.7 | R |
| CDC47 homolog (MCM7) | D55716 | 9.6 | R |
| CDC21 homolog (MCM4) | X74794 | 2.7 | R |
| CDC45 homolog (Porc-PI) | AJ223728 | 4.1 | R |
| HsORC1 (origin recognition complex 1) | U40152 | 2.7 | R |
| DNA polymerase α | X06745 | 2.8 | R |
| Replication factor C (37-kD subunit) | M87339 | 2.6 | |
| B-MYB | X13293 | 9.1 | |
| HPV16 E1 protein binding protein | U96131 | 3.7 | |
| Topoisomerase IIα | J04088 | 8.6 | R |
| Chromatin assembly factor-I (p60 subunit) | U20980 | 2.7 | R |
| High-mobility group chromosomal protein 2 | X62534 | 3.7 | R |
| High-mobility group chromosomal protein 1 | D63874 | 3.6 | R |
| Histone H2A.F/Z variant | AA203494 | 2.8 | |
| Associated with DNA repair: | | | |
| XRCC9 | U70310 | 3.6 | R |
| RAD54 homolog | X97795 | 5.4 | R |
| HEX1 5'-3' exonuclease (RAD2 homolog) | AF042282 | 5.2 | R |
| ATP-dependent DNA ligase I | M36067 | 2.5 | R |
| RAD21 homolog | D38551 | 2.9 | R |
| Associated with transcription and RNA processing: | | | |
| Putative transcription factor CA150 | AF017789 | 2.8 | |
| Transcriptional coactivator ALY | AF047002 | 3.3 | |
| WHSC1/MMSET (SET domain protein) | M401245 | 2.9 | |
| NN8-4AG (SET domain protein) | U50383 | 2.8 | |
| EZH2 (enhancer of zeste homolog 2) | U61145 | 2.8 | |
| PTB-associated splicing factor | X70944 | 2.5 | |
| AU-rich element RNA-binding protein AUF1 | U02019 | 2.8 | |
| U-snRNP-associated cyclophilin | AF016371 | 2.8 | |
| Other genes: | | | |
| 3-phosphoglycerate dehydrogenase | AF006043 | 4.8 | |
| L-type amino acid transporter, subunit LAT1 | M80244 | 4.1 | R |
| Hyaluronan-mediated motility receptor | U29343 | 4 | |
| Phorbolin I (PKC-inducible) | U03891 | 3.9 | |
| PSD-95 binding family protein | D13633 | 3.7 | R |
| HTRIP (TNF receptor component) | U77845 | 3.6 | |
| NAD-dependent methylenetetrahydrofolate dehydrogenase | X16396 | 3.4 | |
| Membrane glycoprotein 4F2 antigen heavy chain | J02939 | 3.2 | |
| Mucin-like protein | D79992 | 3.2 | |
| MAC30 (differentially expressed in meningiomas) | L19183 | 2.9 | |
| P52rIPK (regulator of interferon-induced protein kinase) | AF007393 | 2.8 | |
| Putative phosphoserine aminotransferase | AA192483 | 2.8 | |
| Glucose 6-phosphate translocase | Y15409 | 2.7 | |
| Calcyclin binding protein | AF057356 | 2.6 | |
| Ornithine decarboxylase 1 | X16277 | 2.6 | R |
| Trophinin assisting protein (tastin) | U04810 | 2.5 | |
| Acyl-coenzyme A cholesterol acyltransferase | L21934 | 2.5 | |
| Pinin/SDK3 | Y10351 | 2.5 | |
| Genes with unknown function: | | | |
| EST | AA975298 | 2.7 | |
| EST | AA034414 | 2.5 | |
| EST | AA482549 | 2.5 | |

TABLE 1-continued

Genes downregulated by p21 induction

B. p21-inhibited genes identified by RT-PCR:

| Genes | Accession No. | UniGemV result[b] |
|---|---|---|
| Cyclin A1 | U66838 | IS |
| Cyclin B1 | M25753 | IS |
| CDC25A | NM_001789 | A |
| Dihydrofolate reductase | J00140 | 1.5 |
| ING1 | NM_005537 | A |

[a]Abbreviations: R, RT-PCR; W, western blotting
[b]Abbreviations: IS, insufficient signal; A, absent from the array

TABLE 2

Genes upregulated by p21 induction

| Genes | Accession No | Balanced Diff Expr | Confirmed by[a] |
|---|---|---|---|
| Secreted proteins and proteins associated with extracellular matrix: | | | |
| Fibronectin 1 | X02761 | 5.7 | R |
| Plasminogen activator inhibitor, type I | M14083 | 3.7 | R, N |
| Plasminogen activator, tissue type | M15518 | 2.8 | Z |
| Laminin β2 | X79683 | 2.1 | |
| Desmocollin 2a/bb | X56807 | 3.5 | |
| Podocalyxin-like protein | U97519 | 2 | |
| Activin A (inhibin βA) | J03634 | 2 | R |
| Galectin 3 (Mac-2) | AB006780 | 2.4 | N |
| Mac-2 binding protein | L13210 | 2 | R, N |
| Prosaposin | J03077 | 2.9 | N |
| CTGF (connective tissue growth factor) | M92934 | 3.3 | N |
| Granulin/epithelin | AF055008 | 2.1 | N |
| Cathepsin B | L04288 | 2.4 | N |
| Tissue transglutaminase | M55153 | 2.5 | R, N, W |
| P37NB (slit homolog) | U32907 | 2.1 | |
| Serum amyloid A protein precursor | M26152 | 4 | R, N, W |
| Alzheimer's disease amyloid A4 protein precursor | D87675 | 2 | R, N |
| Complement C3 precursor | K02765 | 5.9 | R, N |
| Testican | X73608 | 2.1 | N |
| Integrin β3 | M35999 | 2.1 | R, N |
| Lysosomal proteins: | | | |
| N-acetylgalactosamine-6-sulfate sulfatase | U06088 | 2.3 | N |
| Acid alpha-glucosidase | X55079 | 2.4 | N |
| Acid lipase A (cholesterol esterase) | X76488 | 2.1 | N |
| Lysosomal pepstatin-insensitive protease (CLN2) | AF017456 | 2.5 | |
| Mitochondrial proteins: | | | |
| Superoxide dismutase 2 | X07834 | 3.5 | R, N, W |
| Metaxin | J03060 | 3.4 | |
| 2,4-dienoyl-CoA reductase | U78302 | 2 | |
| Other genes associated with stress response and signal transduction: | | | |
| Ubiquitin-conjugating enzyme (UbcH8) | AF031141 | 2 | |
| Ubiquitin-specific protease 8 | D29956 | 2 | |
| RTP/Cap43/Drg1/Ndr1 (Inducible by nickel, retinoids, homocysteine and ER stress) | D87953 | 2.5 | |
| C-193 muscle ankyrin-repeat nuclear protein (cytokine-inducible) | X83703 | 3 | |
| LRP major vault protein associated with multidrug resistance | X79882 | 2.2 | N |
| β-arrestin related HHCPA78 homolog (upregulated by vitamin D3) | S73591 | 4.1 | N |
| R-RAS | M14949 | 2.4 | |
| RAB 13 small GTPase | X75593 | 2.2 | |
| P66 SHC (ski oncogene) | U73377 | 2 | N |
| MK-STYX (MAP kinase phosphatase-like protein) | N75168 | 2 | |
| H73 nuclear antigen/MA-3 apoptosis-related/TIS (topoisomerase-inhibitor suppressed) | U96628 | 2.4 | |
| Other genes: | | | |
| Natural killer cells protein 4 | M59807 | 4.4 | R |
| TXK tyrosine kinase (T-cell specific) | L27071 | 3.8 | |

TABLE 2-continued

Genes upregulated by p21 induction

| Genes | Accession No | Balanced Diff Expr | Confirmed by[a] |
|---|---|---|---|
| X-linked PEST-containing transporter | U05321 | 2.1 | |
| AMP deaminase 2 | M91029 | 2 | N |
| FIP2/HYPL huntingtin-interacting protein | AF061034 | 2 | |
| DNASE I homolog | X90392 | 2.5 | N |
| Transcription factor 11 | X77366 | 2 | |
| Histone H2A.2 | L19779 | 2.8 | |
| Histone H2B | AL021807 | 2.4 | |
| Genes with unknown function: | | | |
| 23808 | AF038192 | 2.1 | |
| CGI-147 | AA307912 | 2.1 | N |
| EST | W89120 | 2.8 | |
| EST | A1026140 | 2.5 | |
| EST | AA218982 | 2.4 | |
| EST | W63684 | 2 | |

[a]Abbreviations: R, RT-PCR; N, northern hybridization; W, western blotting; Z, zymography

We claim:

1. A method for identifying a compound that inhibits p21-mediated modulation of cellular gene expression, the method comprising the steps of:

(a) inducing overexpression of p21 in a mammalian cell, (b) assaying the cell in the presence and absence of the compound for changes in expression of a cellular gene whose expression is modulated by p21, wherein the cellular gene is CDC2 (Acc. No. X05360), CKsHs1 (CDC2 kinase)(Acc. No. X54941), PLk1 (polo-like kinase) (Acc. No. U01038), XCAP-H condensin homolog (Acc. No. D38553), CENP-A (centromere protein A) (Acc. No. U14518), CENP-F (centromere protein F) (Acc. No. U30872), MAD2 (Acc. No. U65410), BUBR1 (Acc. No. AF053306), MCAK (mitotic centromere-associated kinesin) (Acc. No. U63743), HSET kinesin-like protein (Acc. No. AL021366), CHL1 helicase (Acc. No. U75968), AIK-1 (auror-a/IPL1-related kinase) (Acc. No. D84212), AIM-1 (AIK-2; aurora/IPL1-related kinase) (Acc. No. AF004022), PRC1 (protein regulating cytokinesis 1) (Acc. No. AF044588), Citron kinase (Acc. No. H10809), Lamin B1 (Acc. No. L37747), Lamin B2 (Acc. No. M94362), LAP-2 (lamin-associated protein 2) (Acc. No. U18271), MPP2 (M phase phosphoprotein 2) (Acc. No. U74612), MPP5 (M phase phosphoprotein 5) (Acc. No. X98261), Thymidine kinase 1 (Acc. No. K02581), Thymidylate synthase (Acc. No. X02308), Uridine phosphorylase (Acc. No. X90858), Ribonucleotide reductase M1 (Acc. No. X59543), Ribonucleotide reductase M2 (Acc. No. X59618), CDC47 homolog (MCM7) (Acc. No. D55716) CDC21 homolog (MCM4) (Acc. No. X74794), CDC45 homolog (Porc-PI) (Acc. No. AJ223728), HsORC1 (origin recognition complex 1) (Acc. No. U40152), DNA polymerase α (Acc. No. X06745), Replication factor C (37-kD subunit) (Acc. No. M87339), B-MYB (Acc. No. X13293), HPV16 E1 protein binding protein (Acc. No. U96131), Topoisomerase IIα (Acc. No. J04088), Chromatin assembly factor-1 (p60 subunit) (Acc. No. U20980), High-mobility group chromosomal protein 2 (Acc. No. X62534), High-mobility group chromosomal protein 1 (Acc. No. D63874), Histone H2A.F/Z variant (Acc. No. AA203494), XRCC9 (Acc. No. U70310), RAD54 homolog (Acc. No. X97795), HEX1 5'-3'exonuclease (RAD2 homolog) (Acc. No. AF042282), ATP-dependent DNA ligase I (Acc. No. M36067), RAD21 homolog (Acc. No. D38551 ), Putative transcription factor CA150 (Acc. No. AF017789), Transcriptional coactivator ALY (Acc. No. AF047002), WHSC1/MMSET (SET domain protein) (Acc. No. AA401245), NN8-4AG (SET domain protein) (Acc. No. U50383), EZH2 (enhancer of zeste homolog 2) (Acc. No. U61145), PTB-associated splicing factor (Acc. No. X70944), AU-rich element RNA-binding protein AUF1 (Acc. No. U02019), U-snRNP-associated cyclophilin (Acc. No. AF016371), 3-phosphoglycerate dehydrogenase (Acc. No. AF006043), L-type amino acid transporter, subunit LAT1 (Acc. No. M80244), Hyaluronan-mediated motility receptor (Acc. No. U29343), Phorbolin I (PKC-inducible) (Acc. No. U03891), PSD-95 binding family protein (Acc. No. D13633), HTRIP (TNF receptor component) (Acc. No. U77845), NAD-dependent methylenetetrahydrofolate dehydrogenase (Acc. No. X16396), Membrane glycoprotein 4F2 antigen heavy chain (Acc. No. J02939), Mucin-like protein (Acc. No. 079992), M:AC30 (differentially expressed in meningiomas) (Acc. No. L19183), P52rIPK (regulator of interferon-induced protein kinase) (Acc. No. AF007393), Putative phosphoserine aminotransferase (Acc. No. AA192483), Glucose 6-phosphate translocase (Acc. No. Y15409), Calcyclin binding protein (Acc. No. AF057356), Ornithine decarboxylase 1 (Acc. No. X16277), Trophinin assisting protein (tastin) (Acc. No. U04810), Acyl-coenzyme A cholesterol acyltransferase (Acc. No. L21934), Pinin/SDK3 (Acc. No. Y10351), EST (Acc. No. AA975298), EST (Acc. No. AA034414), EST (Acc. No. AA482549) Cyclin A1 (Acc. No. U66838), Cyclin B1 (Acc. No. M25753), CDC25A (Acc. No. NM001789), Dihydrofolate reductase (Acc. No. J00140), or ING1 (Acc. No. NM 005537), Fibronectin 1 (Acc. No. X02761), Plasminogen activator inhibitor, type I (Acc. No. M14083), Plasminogen activator, tissue type (Acc. No. M15518), Laminin β2 (Acc. No. X79683), Desmocollin 2a/bb (Acc. No. X56807), Podocalyxin-like protein (Acc. No. U97519), Activin A (inhibin βA) (Acc. No. J03634), Galectin 3 (Mac-2) (Acc. No. AB006780), Mac-2 binding protein (Acc. No. L13210), Prosaposin (Acc. No. J03077), CTGF (connective tissue growth factor) (Acc.

No. M92934), Granulin/epithelin (Acc. No. AF055008), Cathepsin B (Acc. No. L04288), Tissue transglutaminase (Acc. No. M55153), P37NB (slit homolog) (Acc. No. U32907), Serum amyloid A protein precursor (Acc. No. M26152), Alzheimer's disease amyloid A4 protein precursor (Acc. No. D87675), Complement C3 precursor (Acc. No. K02765), Testican (Acc. No. X73608), Integrin β3 (Acc. No. M35999), N-acetylgalactosamine-6-sulfate sulfatase (Acc. No. U06088), Acid alpha-glucosidase (Acc. No. X55079), Acid lipase A (cholesterol esterase) (Acc. No. X76488), Lysosomal pepstatin-insensitive protease (CLN2) (Acc. No. AF017456), Superoxide dismutase 2 (Acc. No. X07834), Metaxin (Acc. No. J03060), 2,4-dienoyl-CoA reductase (Acc. No. U78302), Ubiquitin-conjugating enzyme (UbcH8) (Acc. No. AF031141), Ubiquitin-specific protease 8 (Acc. No. D29956), RTP/Cap43/Drg1/Ndr1(Inducible by nickel, retinoids, homocysteine and ER stress) (Acc. No. D87953), C-193 muscle ankyrin-repeat nuclear protein (cytokine-inducible) (Acc. No. X83703), LRP major vault protein associated with multidrug resistance (Acc. No. X79882), β-arrestin related HHCPA78 homolog (upregulated by vitamin D3) (Acc. No. S73591), R-RAS (Acc. No. M14949), RAB 13 small GTPase (Acc. No. X75593), P66 SHC (ski oncogene) (Acc. No. U73377), MK-STYX (MAP kinase phosphatase-like protein) (Acc. No. N75168), H73 nuclear antigen/MA-3 apoptosis-related/TIS (topoisomerase-inhibitor suppressed) (Acc. No. U96628), Natural killer cells protein 4 (Acc. No. M598071), TXK tyrosine kinase (T-cell specific) (Acc. No. L27071), X-linked PEST-containing transporter (Acc. No. U05321), AMP deaminase 2 (Acc. No. M91029), FIP2/HYPL huntingtin-interacting protein (Acc. No. AF061034), DNASE I homolog (Acc. No. X90392), Transcription factor 11 (Acc. No. X77366), Histone H2A.2 (Acc. No. L19779), Histone H2B (Acc. No. AL021807), 23808 (Acc. No. AF038192), CGI-147 (Acc. No. AA307912), EST (Acc. No. W89120), EST (Acc. NO. AI026140), EST (Acc. No. AA218982), or EST (Acc. No. W63684); and (c) identifying the compound as an inhibitor of p21-mediated modulation of cellular gene expression if expression of the cellular gene of subpart (b) is changed to a lesser extent in the present of the compound than in the absence of the compound.

2. The method of claim 1, wherein the mammalian cell comprises a recombinant expression construct encoding a mammalian p21 gene transcriptionally controlled by an inducible heterologous promoter and p21 overexpression is produced by contacting the cell with an inducing agent that induces transcription from the inducible promoter or removing an agent that inhibits transcription from the promoter.

3. The method of claim 1, wherein expression of the cellular gene is repressed by p21.

4. The method of claim 1, wherein expression of the cellular gene is induced by p21.

5. The method of claim 1, wherein expression of the cellular gene is detected using an immunological reagent.

6. The method of claim 1, wherein expression of the cellular gene is detected by assaying for an activity of the cellular gene product.

7. The method of claim 1, where expression of the cellular gene is detected by hybridization to a complementary nucleic acid.

8. A method for identifying a compound that potentiates the effects of p21-mediated modulation of cellular gene expression, the method comprising the steps of:

(a) inducing overexpression of p21 in a mammalian cell;
(b) assaying the cell in the presence and absence of the compound for changes in expression of a cellular gene whose expression is induced or repressed by p21, wherein the cellular gene is CDC2 (Acc. No. X05360), CKsHs1 (CDC2 kinase) (Acc. No. X54941) PLK1 (polo-like kinase) (Acc. No. U01038) XCAP-H condensin homolog (Acc. No. D38553,) CENP-A (centromere protein A) (Acc. No. U14518), CENP-F (centromere protein F) (Acc. No. U30872), MAD2 (Acc. No. U65410), BUBR1 (Acc. No. AF053306), MCAK (mitotic centromere-associated kinesin) (Acc. No. U63743), HSET kinesin-like protein (Acc. No. AL021366), CHL1 helicase (Acc. No. U75968), AIK-1 (aurora/IPL1-related kinase) (Acc. No. D84212) AIM-1 (AIK-2, aurora/IPL1-related kinase) (Acc. No. AF004022). PRC1 (protein regulating cytokinesis 1) (Acc. No. AF044588), Citron kinase (Acc. No. H10809), Lamin B1 (Acc. No. L37747), Lamin B2 (Acc. No. M94362), LAP-2 (lamin-associated protein 2) (Acc. No. U18271), MPP2 (M phase phosphoprotein 2) (Acc. No. U74612), MPP5 (M phase phosphoprotein 5) (Acc. No. X98261), Thymidine kinase 1 (Acc. No. K02581), Thymidylate synthase (Acc. No. X02308), Uridine phosphorylase (Acc. No. X90858), Ribonucleotide reductase M1 (Acc. No. X59543), Ribonucleotide reductase M2 (Acc. No. X59618) CDC47 homolog (MCM7) (Acc. No. D55716), CDC21 homolog (MCM4) (Acc. No. X74794), CDC45 homolog (PorcPI) (Acc. No. AJ223728), HsORC1 (origin recognition complex 1) (Acc. No. U40152), DNA polymerase α (Acc. No. X06745). Replication factor C (37-kD subunit) (Acc. No. M87339), B-MYB (Acc. No. X13293), HPV16 E1 protein binding protein (Acc. No. U96131), Topoisomerase IIα (Acc. No. J04088), Chromatin assembly factor-I (p60 subunit) (Acc. No. U20980), High-mobility group chromosomal protein 2 (Acc. No. X62534), High-mobility group chromosomal protein 1 (Acc. No. D63874), Histone H2A.F/Z variant (Acc. No. AA203494), XRCC9 (Acc. No. U70310), RAD54 homolog (Acc. No. X97795), HEX1 5'-3'exonuclease (RAD2 homolog) (Acc. No. AF042282), ATP-dependent DNA ligase I (Acc. No. M36067), RAD21 homolog (Acc. No. D38551), Putative transcription factor CA150 (Acc. No. AF017789), Transcriptional coactivator ALY (Acc. No. AF047002), WHSC1/MMSET (SET domain protein) (Acc. No. AA401245), NN8-4AG (SET domain protein) (Acc. No. U50383), EZH2 (enhancer of zeste homolog 2) (Acc. No. U61145), PTB-associated splicing factor (Acc. No. X70944), AU-rich element RNA-binding protein AUF1 (Acc. No. U02019), U-snRNP-associated cyclophilin (Acc. No. AF016371), 3-phosphoglycerate dehydrogenase (Acc. No. AF006043), L-type amino acid transporter, subunit LAT1 (Acc. No. M80244), Hyaluronan-mediated motility receptor (Acc. No. U29343), Phorobolin I (PKC-inducible) (Acc. No. U03891), PSD-95 binding family protein (Acc. No. D13633), HTRIP (TNF receptor component) (Acc. No. U77845), NAD-dependent methylenetetrahydrofolate dehydrogenase (Acc. No. X16396), Membrane glycoprotein 4F2 antigen heavy chain (Acc. No. J02939), Mucin-like protein (Acc. No. 079992), MAC30 (differentially expressed in meningiomas) (Acc. No. L19183), P52rIPK (regulator of interferon-induced protein kinase) (Acc. No. AF007393), Putative phosphoserine aminotransferase (Acc. No. AA192483), Glucose 6-phosphate translocase (Acc. No. Y15409), Calcyclin binding protein (Acc. No. AF057356), Ornithine decarboxylase 1 (Acc. No. X16277), Trophinin assisting protein (tastin) (Acc. No. U04810), Acyl-coenzyme A cholesterol acyltransferase (Acc. No. L21934), Pinin/SDK3 (Acc. No. Y10351), EST (Acc. No. AA975298), EST (Acc. No. AA034414), EST (Acc. No. AA482549), Cyclin A1 (Acc. No. U66838), Cyclin B1 (Acc. No. M25753), CDC25A (Acc. No. NM 001789), Dihydrofolate reductase (Acc. No. J00140), or ING1 (Acc. No. NM 005537) Fibronectin 1 (Acc. No. X02761), Plasminogen activator inhibitor, type I (Acc. No. M14083), Plasminogen activator tissue type (Acc. No. M15518), Laminin β2 (Acc. No. X79683), Desmocollin 2a/bb (Acc. No. X56807), Podocalyxin-like protein (Acc. No. U97519), Activin A (inhibin βA) (Acc. No. J03634), Galectin 3 (Mac-2) (Acc. No. AB006780), Mac-2 binding protein (Acc. No. L13210), Prosaposin (Acc. No. J03077), CTGF (connective tissue growth factor) (Acc. No. M92934), Granulin/epithelin (Acc. No. AF055008), Cathepsin B (Acc. No. L04288), Tissue transglutaminase (Acc. No. M55153), P37NB (slit homolog) (Acc. No. U32907), Serum amyloid A protein precursor (Acc. No. M26152), Alzheimer's disease amyloid A4 protein precursor (Acc. No. D87675), Complement C3 precursor (Acc. No. K02765), Testican (Acc. No. X73608), Integrin β3 (Acc. No. M35999), N-acetylgalactosamine-6-sulfate sulfatase (Acc. No. U06088), Acid alpha-glucosidase (Acc. No. X55079), Acid lipase A (cholesterol esterase) (Acc. No. X76488), Lysosomal pepstatin-insensitive protease (CLN2) (Acc. No. AF017456), Superoxide dismutase 2 (Acc. No. X07834), Metaxin (Acc. No. J03060), 2,4-dienoyl-CoA reductase (Acc. No. U78302), Ubiquitin-conjugating enzyme (UbcH8) (Acc. No. AF031141), Ubiquitin-specific protease 8 (Acc. No. D29956), RTP/Cap43/Drg1/Ndr1 (Inducible by nickel, retinoids, homocysteine and ER stress) (Acc. No. D87953), C-193 muscle ankyrin-repeat nuclear protein (cytokine-inducible) (Acc. No. X83703), LRP major vault protein associated with multidrug resistance (Acc. No. X79882), β-arrestin related HHCPA78 homolog (upregulated by vitamin D3) (Acc. No. S73591), R-RAS (Acc. No. M14949), RAB 13 small GTPase (Acc. No. X75593), P66 SHC (ski oncogene) (Acc. No. U73377), MK-STYX (MAP kinase phosphatase-like protein) (Acc. No. N75168), H73 nuclear antigen/MA-3 apoptosis-related/TIS (topoisomerase-inhibitor suppressed) (Acc. No. U96628), Natural killer cells protein 4 (Acc. No. M59807), TXK tyrosine kinase (T-cell specific) (Acc. No. L27071), X-linked PEST-containing transporter (Acc. No. U05321), AMP deaminase 2 (Acc. No. M91029), FIP2/HYPL huntingtin-interacting protein (Acc. No. AF061034), DNASE 1 homolog (Acc. No. X90392), Transcription factor 11 (Acc. No. X77366), Histone H2A.2 (Acc. No. L19779), Histone H2B (Acc. No. AL021807), 23808 (Acc. No. AF038192), CGI-147 (Acc. No. AA307912), EST (Acc. No. W89120), EST (Acc. No. A1026140), EST (Acc. No. AA218982), or EST (Acc. No. W63684); and (c) identifying the compound as a potentiator of p21-mediated modulation of cellular gene expression if expression of the cellular gene of subpart (b) is induced or repressed to a greater extent in the presence of the compound than in the absence of the compound.

9. The method of claim 8, wherein the mammalian cell comprises a recombinant expression construct encoding a mammalian p21 gene transcriptionally controlled by an inducible heterologous promoter and p21 expression is produced by contacting the cell with an inducing agent that induces transcription from the inducible promoter.

10. The method of claim 8, wherein expression of the cellular gene is repressed by p21.

11. The method of claim 8, wherein expression of the cellular gene is induced by p21.

12. The method of claim 8, wherein expression of the cellular gene is detected using an immunological reagent.

13. The method of claim 8, wherein expression of the cellular gene is detected by assaying for an activity of the cellular gene product.

14. The method of claim 8, where expression of the cellular gene is detected by hybridization to a complementary nucleic acid.

15. The method of claim 8, wherein p21 is produced in the cell to an extent that its effect is less than the maximum effect of p21 expression in the cell.

* * * * *